United States Patent [19]
Fahy

[11] Patent Number: 5,472,876
[45] Date of Patent: Dec. 5, 1995

[54] COMPUTER CONTROLLED CRYOPROTECTANT PERFUSION APPARATUS

[75] Inventor: Gregory M. Fahy, Gaithersburg, Md.

[73] Assignee: The American National Red Cross, Rockville, Md.

[21] Appl. No.: 375,469

[22] Filed: Jan. 19, 1995

Related U.S. Application Data

[60] Continuation of Ser. No. 29,432, Mar. 10, 1993, abandoned, which is a division of Ser. No. 725,054, Jul. 8, 1991, Pat. No. 5,217,860.

[51] Int. Cl.⁶ .................................................. A01N 1/02
[52] U.S. Cl. ......................................... 435/284.1; 435/1.2
[58] Field of Search ................................ 435/283, 1, 2; 436/176

[56] References Cited

U.S. PATENT DOCUMENTS

| | | | |
|---|---|---|---|
| 3,639,084 | 2/1972 | Goldhaber | 435/283 X |
| 3,753,865 | 8/1973 | Belzer et al. | 435/283 |
| 3,772,153 | 11/1973 | De Rassart | 435/283 X |
| 3,843,455 | 10/1974 | Bier | 435/283 |
| 3,892,628 | 7/1975 | Thorne et al. | 435/283 |
| 3,914,954 | 11/1975 | Doerig | 62/306 |
| 3,995,444 | 12/1976 | Clark et al. | 435/283 |
| 4,559,298 | 12/1985 | Fahy | 435/1 |
| 4,618,586 | 10/1986 | Walker | 435/1 |
| 4,629,686 | 12/1986 | Gruenberg | 435/1 |
| 4,704,029 | 11/1987 | Van Heuvelen | 436/95 X |
| 4,837,390 | 6/1989 | Reneau | 435/283 X |
| 5,051,352 | 9/1991 | Martindale et al. | 435/283 X |
| 5,141,847 | 8/1992 | Sugimachi et al. | 435/1 |

OTHER PUBLICATIONS

Adem et al., J. Biomed. Engng. 3:134–139 (1981).
Armitage et al., Cryobiology 18:370–377 (1981).
Belzer et al., Organ Perfusion and Preservation (J. C. Norman et al., editors), Appleton–Century–Crofts, New York, 1968, pp. 3–12.
Fahy, G. M. Cryo–Letters 1:312–317 (1980).
Fahy et al., Cryo–Letters 5:33–46 (1984).
Fahy et al., Cryobiology 21:407, 420, 422 (1984).
Fahy, et al., Cryobiology 22:606–608 (1985).
Jacobsen et al., Cryobiology 15:18–26 (1978).

Primary Examiner—Robert J. Warden
Assistant Examiner—Robert Carpenter
Attorney, Agent, or Firm—Sterne, Kessler, Goldstein & Fox

[57] ABSTRACT

A computer-controlled apparatus and method for perfusing a biological organ, such as a heart, kidney, liver, etc. The apparatus comprises a plurality of fluid reservoirs and an organ container for holding the biological organ. A first fluid flow path is defined as a loop from the plurality of reservoirs to necessary sensors and temperature conditioning means and back to the plurality of reservoirs. The reservoirs are selectively connectable to the first fluid flow path. Pump means are interposed in the first fluid flow path for pumping fluid from the first fluid flow path to a second fluid flow path. The organ container is located in this second fluid flow path. Pump means may also be included in the second fluid flow path for pumping fluid from the organ container to one or more of the reservoirs or to waste. One or more sensors are interposed in the fluid flow paths for sensing at least one of the concentration, temperature, pH, and pressure of the fluid flowing in the first and second fluid flow paths. Measuring means are interposed in the first and second fluid flow paths for measuring concentration and temperature differences between the upstream and downstream sides, in the fluid flow direction, of the organ container. The sensor(s) and the measuring means are connected to a programmable computer for providing a continuous information stream from the sensor(s) to the computer. The computer is coupled to the selection means and the pump means to continuously selectively control (a) the flow of fluid from each of the reservoirs individually to the fluid flow paths, and (b) at least one of the concentration, temperature, pressure and pH of the fluid flowing in the second fluid flow path, in accordance with a predetermined computer program without operator intervention.

17 Claims, 16 Drawing Sheets

OTHER PUBLICATIONS

Jacobsen, IB A., *Cryobiology* 15:302–311 (1978).
Pegg, D. E., *Cryobiology* 9:411–419 (1972).
Pegg et al., *Cryobiology* 14:168–178 (1977).
Pegg, D. E., Banking of Cells, Tissues and Organs at Low Temperatures. In: Current Trends in Cryobiology (A. U. Smith, editor), Plenum Press, NY, 1970, pp. 153–180, but particularly pp. 175–177.

Sadri, F., *Organ Perfusion Systems: An Evaluation Criteria*, T.O.P.S. Medical Corp. (1987).

Sherwood et al., *Organ Preservation*, Churchill Livingstone, London, 1973, Chap. 15, pp. 152–174.

Water Instruments Medical Group, Waters Instrument Inc., Price List, 1982.

Fahy, G. M. "Slide Shown in 1985" (Slide of Perfusion Apparatus shown publicly at a conference), 1985.

FROM FIG.6C

```
┌─────────────────────────────────────────────────────────────────┐
│  AT PREDETERMINED POINTS, BEGIN AND FINALLY END                 │
│  TEMPERATURE RISE AS CONCENTRATION FALLS                        │
└─────────────────────────────────────────────────────────────────┘
                              ↓
┌─────────────────────────────────────────────────────────────────┐
│  UPON REACHING A PREDETERMINED THRESHOLD CONCENTRATION THAT     │
│  OCCURS NEAR THE TIME R3's INNER CHAMBER WOULD OTHERWISE        │
│  BECOME EMPTY, TURN OFF OR SLOW DOWN GRADIENT PUMP              │
└─────────────────────────────────────────────────────────────────┘
                              ↓
┌─────────────────────────────────────────────────────────────────┐
│  ACTIVATE CUSTOMIZED S32 DUTY CYCLE SO AS TO INTRODUCE FLUID    │
│  FROM R3's OUTER CHAMBER TO R3's INNER CHAMBER SLOWLY AT FIRST  │
│  AND THEN MORE AND MORE RAPIDLY SO AS TO REDUCE CONCENTRATION   │
│  IN R3's INNER CHAMBER SLOWLY IN ACCORDANCE WITH PREDETERMINED  │
│  SCHEDULE; IN TANDEM WITH THIS, PHASE GRADIENT PUMP BACK IN AND/OR │
│  CEASE FULL RECIRCULATION TO R3 IN ORDER TO REDUCE RETURN OF    │
│  CRYOPROTECTANT TO R3 FROM THE CIRCUIT AND ORGAN                │
└─────────────────────────────────────────────────────────────────┘
                              ↓
┌─────────────────────────────────────────────────────────────────┐
│  WHEN CONCENTRATION IS SUFFICIENTLY CLOSE TO OR EQUAL TO ZERO,  │
│  JUMP TO R4 (WHICH CONTAINS NO CRYOPROTECTANT AND LITTLE OSMOTIC BUFFER); │
│  IF APPROPRIATE, PHASE IN RECIRCULATION TO R4 AS WAS DONE FOR R2 AND R3 ABOVE │
└─────────────────────────────────────────────────────────────────┘
                              ↓
┌─────────────────────────────────────────────────────────────────┐
│  IF APPROPRIATE, AFTER DESIRED PERIOD, ACTIVATE R4's SOLENOID VALVE AND │
│  WASH OUT OSMOTIC BUFFER TO DESIRED DEGREE; ADJUST CALIBRATION TO │
│  DISPLAY THE WASHOUT OF THE OSMOTIC BUFFER                      │
└─────────────────────────────────────────────────────────────────┘
                              ↓
┌─────────────────────────────────────────────────────────────────┐
│  SIGNAL OPERATOR THAT ORGAN IS READY FOR REMOVAL FROM THE PERFUSION │
│  MACHINE AND NOW CAN BE TRANSPORTED OR TRANSPLANTED; CONTINUE TO │
│  MAINTAIN ORGAN PERFUSION PARAMETERS UNTIL LARGE DROP IN PRESSURE IS │
│  SENSED AS THE ORGAN IS REMOVED FROM THE CIRCUIT                │
└─────────────────────────────────────────────────────────────────┘
                              ↓
                         TO FIG.6E
```

FIG.6D

FROM FIG.6D

UPON PRESSURE DROP, CAPTURE DATA SCREEEN AS AN IMAGE, CLOSE THE DIGITAL DATA FILE(S) AND COPY THEM TO BACKUP MEDIA AND/OR TO ALTERNATE STORAGE LOCATION, SIGNAL OPERATOR TO ATTEND TO ANY REQUIRED SHUT-DOWN PROCEDURES, THEN TERMINATE PROGRAM [RESERVOIR PURGING, PRIMING, AND SYSTEM CLEANING ARE ACCOMPLISHED BY SATELLITE PROGRAMS]

FIG.6E

FROM FIG.7A

MEANWHILE, IF GRADUAL DRUG ADDITION IS TO BE ACCOMPLISHED USING R1, ACTIVATE GRADIENT FORMER TO APPROPRIATE RATE; RECORD DRUG CONCENTRATION AND/OR MEDIATOR RELEASE FROM ORGAN IN RESPONSE TO DRUG IF DESIRED AND POSSIBLE

↓

OCCASIONALLY RECHECK PRESSURE TRANSDUCER ACCURACY AND UPDATE ITS CALIBRATION ACCORDINGLY

↓

SWITCH TO R2; RECIRCULATION TO R2 CAN CEASE IF A STEP CHANGE IN CALCIUM, DRUG, AUTOCOID, BLOOD, OR SERUM CONCENTRATION FROM ZERO OR BASELINE IS BEING EFFECTED; IF R2's ROLE IS TO STABILIZE A PREVIOUSLY-ESTABLISHED CONCENTRATION, FLUID RECIRCULATION TO R2 NEED NOT BE INTERRUPTED; IF PROTOCOL INVOLVES TEMPERATURE CHANGES, SUCH AS PERFUSION AT NORMOTHERMIA WITH BLOOD, TEMPERATURE CHANGE IS ALSO IMPOSED AT ABOUT THE SAME TIME [FOR BLOOD PERFUSION, AN AUXILIARY HEAT EXCHANGER IS USED TO WARM THE BLOOD PRIOR TO ITS ENTRY INTO THE CIRCUIT PUMP HEAD, AND THE AUXILIARY FILTER ACCESSED BY S4 AND S5 IS A BLOOD FILTER]

↓

IF APPROPRIATE, RESTORE RECIRCULATION (TO R2) AFTER CONTAMINATING SOLUTION FROM R1 HAS BEEN ELIMINATED FROM THE REST OF THE CIRCUIT; THIS CAN BE DONE FIRST FROM THE REFRACTOMETER LOOP AND SECOND FROM THE ORGAN LOOP TO MINIMIZE BOTH FLUID WASTE AND CONTAMINATION

↓

IF APPROPRIATE, SET TIME OF SWITCH TO R3 AND PROCEED SIMILARLY THROUGH R3 AND, IF DESIRED, R4, DEPENDING ON THE DESIGN OF THE EXPERIMENT; FOR SOME EXPERIMENTS, R4 MAY CONTAIN FIXATIVE.

↓

AFTER CYCLING THROUGH ALL DESIRED RESERVOIRS THE DESIRED NUMBER OF TIMES, INFORM THE OPERATOR THAT THE PERFUSION IS COMPLETED AND THE ORGAN IS READY TO REMOVE

↓

WHEN PRESSURE FALLS IN RESPONSE TO ORGAN REMOVAL, CLOSE DATA FILES, CAPTURE SCREEN AS AN IMAGE, DUMP SCREEN TO HARD COPY IF DESIRED BY OPERATOR, SET ALL PUMP SPEEDS TO ZERO, PROVIDE ANY FINAL INSTRUCTIONS TO USER, AND TERMINATE PROGRAM

FIG.7B

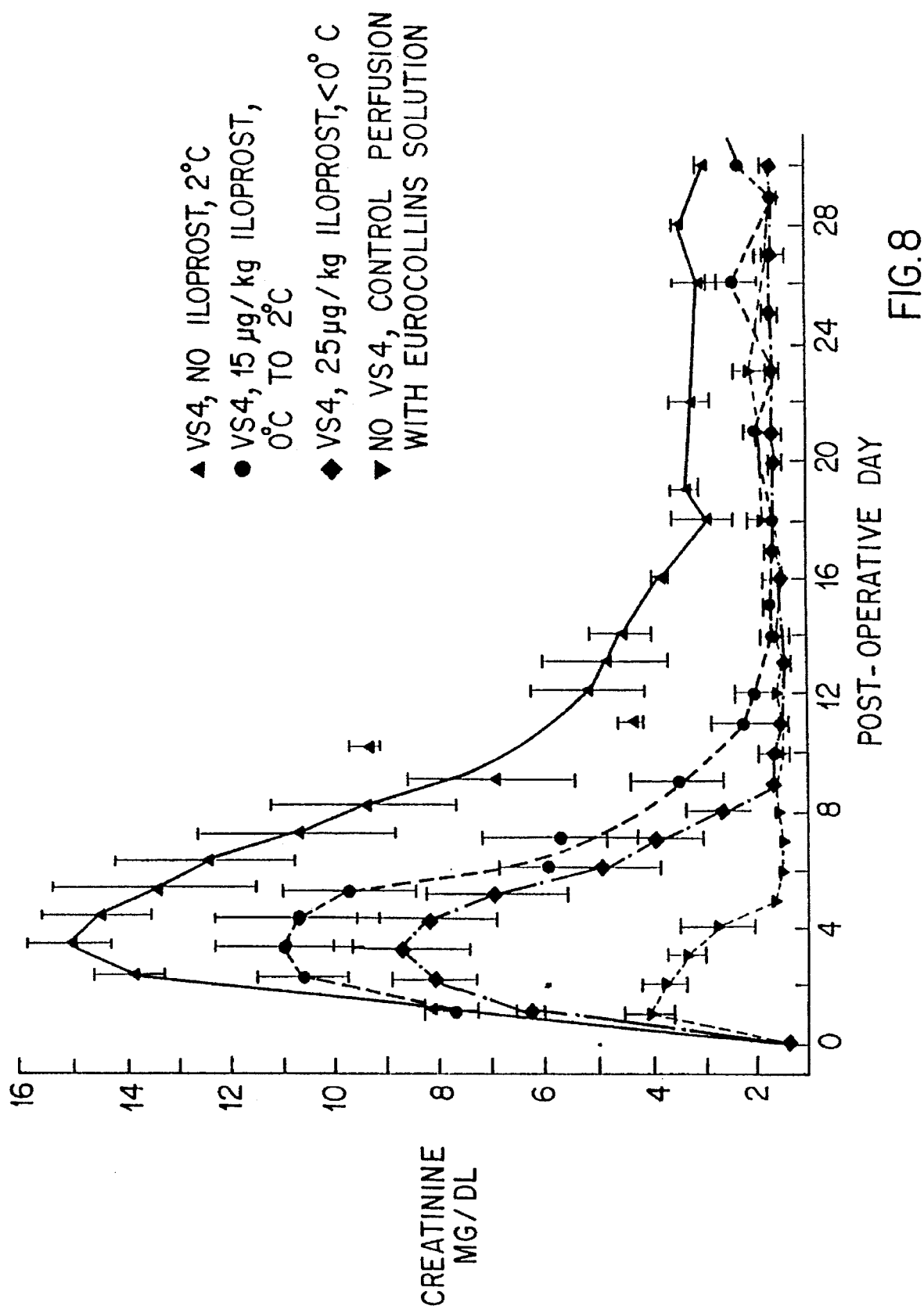

COMPUTER CONTROLLED CRYOPROTECTANT PERFUSION APPARATUS

This application is a continuation, of application Ser. No. 08/029,432, filed Mar. 10, 1993, now abandoned, which is a divisional, of application Ser. No. 07/725,054, filed Jul. 8, 1991, now U.S. Pat. No. 5,217,860.

FIELD OF THE INVENTION

This invention relates to the field of organ perfusion. More particularly, it relates to a computer controlled apparatus and method for perfusing isolated animal, and more specifically, human, organs. Still more particularly, this invention relates to an apparatus and method for introducing and removing vitrifiable concentrations of cryoprotective agents into and from isolated organs or tissues for preservation and subsequent use.

BACKGROUND OF THE INVENTION

Cryopreservation (that is, preservation at very low temperatures) of organs would allow organ banks to be established for transplant surgeons in much the same way blood banks serve the medical community today. The main difficulty with cryopreservation is that it requires the perfusion of organs with high concentrations of cryoprotective agents (water soluble organic molecules that minimize or prevent freezing injury during cooling to very low temperatures). No fully suitable equipment or process has been developed to date for carrying out this perfusion process. This has prevented the establishment of viable organ banks that could potentially save lives.

Devices and methods for perfusing organs with cryoprotectant have been described in the literature since the early 1970's. See, Pegg, D. E., Banking of Cells, Tissues, and Organs at Low Temperatures, Current Trends in Cryobiology, A. U. Smith, Editor, Plenum Press, New York, 1970: pp. 153–180, but particularly pages 175–177; and Pegg, D. E., Perfusion of Rabbit Kidneys with Cryoprotective Agents, Cryobiology 9:411–419, 1972).

In the apparatus initially described by Pegg, two perfusion circuits operated simultaneously, one with and one without cryoprotectant. Cryoprotectant was introduced and removed by abruptly switching from the cryoprotectant-free circuit to the cryoprotectant-containing circuit, then back again. The pressure was controlled by undescribed techniques, and data was fed into a data logger which provided a paper tape output which was processed by a programmable desk-top Wang calculator. The experimental results were poor. The equipment and technique described were considered inadequate by Pegg and his colleagues, who later modified them considerably.

In 1973, G. J. Sherwood and J. R. Flower, in: Organ Preservation (D. E. Pegg, editor, Churchill Livingstone, London, 1973, pp. 152–174), described four potential perfusion systems, none of which are known to have been built. The first system consisted of a family of reservoirs connected directly to the organ via a multiway valve, changes being made in steps simply by switching from one reservoir to another.

The second system created changes in concentration by metering flow from a diluent reservoir and from a cryoprotectant concentrate reservoir into a mixing chamber and then to the kidney. No separate pump for controlling flow to the kidney was included. Total flow was controlled by the output of the metering pumps used for mixing. A heat exchanger was used before rather than after the filter, and there was an absence of any arterial sensing. As will become readily apparent below, the only similarity between this system and the present invention was the use of two concentration sensors, one in the arterial line and one in the venous line of the kidney. Organ flow rate was forced to vary in order to minimize A-V concentration differences. The sensing of concentration before and after the kidney in the circuit is analogous to but substantially inferior to the use of a refractometer and a differential refractometer in the present invention. The present inventors' experience has shown that the use of a differential refractometer is necessary for its greater sensitivity. The concept of controlling organ A-V gradient by controlling organ flow is distinctly inferior to the system of the present invention.

The third system described by Sherwood et al. also lacked a kidney perfusion pump, relying on a "backpressure control valve" to recirculate perfusate from the filter in such a way as to maintain the desired perfusion pressure to the kidney. As with the second Sherwood system, the heat exchanger is proximal to the filter and no bubble trap is present. The perfusate reservoir's concentration is controlled by metered addition of cryoprotectant or diluent as in the second Sherwood system, and if flow from the organ is not recirculated, major problems arise in maintaining and controlling perfusate volume and concentration. None of these features is desirable.

The fourth system was noted by Pegg in an appendix to the main paper. In this system, perfusate is drained by gravity directly from the mixing reservoir to the kidney through a heat exchanger, re-entering the reservoir after passing through the kidney. Concentration is sensed also by directly and separately pumping liquid from the reservoir to the refractometer and back.

Modifications and additional details were reported in 1977 (Pegg, D. E., and Wusteman, M. T., Perfusion of Rabbit Kidneys with Glycerol Solutions at 5° C.). The apparatus used one mixing reservoir and one reservoir for adding glycerol concentrate or glycerol-free perfusate to the mixing reservoir to control concentration. The volume of the mixing reservoir was held constant during perfusion, necessitating an exponentially increasing rate of diluent addition during cryoprotectant washout to maintain a linear rate of concentration change. The constant mixing reservoir volume and the presence of only a single delivery reservoir also made it impossible to abruptly change perfusate concentration. All components of the circuit other than the kidney and a pre-kidney heat exchanger were located on a lab bench at ambient temperature, with the reservoir being thermostatted at a constant 30° C. The kidney and the heat exchanger were located in a styrofoam box whose internal temperature was not controlled. Despite this lack of control of the air temperature surrounding the kidney, only the arterial temperature but not the venous temperature or even the kidney surface temperature was measured. The use of a styrofoam box also did not allow for perfusion under sterile conditions. The only possible way of measuring organ flow rate was by switching off the effluent recirculation pump and manually recording the time required for a given volume of fluid to accumulate in the effluent reservoir, since there was no perfusion pump which specifically supplied the organ, unlike the present invention. Pressure was controlled, not on the basis of kidney resistance, but on the basis of the combined resistance of the kidney and a manually adjustable bypass valve used to allow rapid circulation of perfusate through the heat exchanger and back to the mixing reservoir.

The pressure sensor was located at the arterial cannula, creating a fluid dead space requiring manual cleaning and potentially introducing undesired addition of unmixed dead space fluid into the arterial cannula. Pressure control was achieved by means of a specially-fabricated pressure control unit whose electrical circuit was described in an earlier paper (D. E. Pegg and C. J. Green, Renal Preservation by Hypothermic Perfusion. 1. The importance of pressure-control, Cryobiology 10:56–66, 1973). Arterial concentration but not venous concentration was measured. No computer control or monitoring was used. Concentration was controlled by feeding the output of the recording refractometer into a "process controller" for comparison to the output of a linear voltage ramp generator and appropriate adjustment of concentrate or diluent flow rate. Glycerol concentrations were measured manually at 5 minute intervals at both the mixing reservoir and the arterial sample port: evidently, the refractometer was not used to send a measurable signal to a recording device. Temperature and flow were recorded manually at 5 minute intervals. Arterial pressure and kidney weight were recorded as pen traces on a strip chart recorder. None of these features is desirable.

Further refinements were reported by Jacobsen, I. A., Pegg, D. E., Wusteman, M. C., and Robinson, S. M., Transplantation of Rabbit Kidneys Perfused with Glycerol Solutions at 10° C., Cryobiology 15:18–26, 1978. A bubble trap was added, the sample port on the kidney bypass was eliminated (concentration was measured at the distal end of the bypass line instead), and temperature was recorded as a trace on a strip chart recorder rather than manually every 5 minutes. Additionally, these authors reported that bypass concentration lagged reservoir concentration by 5 min (v. 3 min or less for arterial concentration in the present invention) and that terminal cryoprotectant concentration could not be brought to less than 70 mM after adding 5 liters of diluent to the mixing reservoir (v. near-zero terminal concentrations in the present invention using less than 3 liters of diluent and using peak cryoprotectant concentrations approximately twice those of Jacobsen et al.).

A variation on the system was also reported the same year by Jacobsen (Jacobsen, I. A., Distribution and Removal of Glycerol by Vascular Albumin Perfusion in Rabbit Kidneys, Cryobiology 15:302–311, 1978). Jacobsen measured but did not report air temperatures surrounding the kidney during perfusion. He reduced the mixing reservoir volume to 70 ml, which was a small fraction of the 400 ml total volume of the circuit. No electronic-output refractometer appears to have been used to directly sense glycerol concentration and control addition and washout. Instead, the calculated values of concentrate or diluent flow rate were drawn on paper with India ink and read by a Leeds and Northrup Trendtrak Programmer which then controlled the concentrate/diluent pump. Despite the low circuit volume, the minimum concentration of cryoprotectant which could be achieved was about 100 mM.

Additional alterations of the same system were reported by Armitage et al. in 1981 (W. J. Armitage, G. Matthes, and D. E. Pegg, Seleno-dl-methionine Reduces Freezing Injury in Hearts Protected with Ethanediol, Cryobiology 18:370–377, 1981). Essentially, the entire perfusion circuit previously used was placed into a refrigerated cabinet. Instead of a voltage ramp controller, a cam-follower was used. Again, however, it was necessary to calculate the required-rates of addition of glycerol or diluent using theoretical equations in order to cut the cam properly, an approach which may introduce errors in the actual achievement of the desired concentration-time histories. Finally, a modification was made in which an additional reservoir was added to the circuit. This reservoir was apparently accessed by manual stopcocks (the mode of switching to and from this reservoir was not clearly explained), and use of the new reservoir was at the expense of being able to filter the perfusate or send it through a bubble trap. The new reservoir was not used to Change cryoprotectant concentration; rather, it was used to change the ionic composition of the medium after the cryoprotectant had been added. The volume of the mixing reservoir was set at 500 ml, allowing a final cryoprotectant concentration of 40 mM to be achieved.

The circuits described above represent the current state of the art of cryoprotectant perfusion by others known to the present inventors.

An approach to organ preservation at cryogenic temperatures previously described by the present inventors involved vitrifying rather than freezing organs during cooling. Vitrification, or solidification without freezing, can be brought about in living systems by replacing large fractions of water in these systems with cryoprotectant agents (also known as cryoprotectants) whose presence inhibits crystallization. In known techniques, however, it has never been possible to use sufficiently high cryoprotectant concentrations without killing the organ. Vitrification typically requires concentrations greater than 6 molar cryoprotectant, whereas the limiting concentration for organ survival is typically about 4 molar.

One type of damage potentially caused by cryoprotectants is osmotic damage. Cryobiologists learned of the osmotic effects of cryoprotectants in the 1950's and of the necessity of controlling these effects so as to prevent unnecessary damage during the addition and removal of cryoprotectants to isolated cells and tissues. Similar lessons were leaned when cryobiologists moved on to studies of whole organ perfusion with cryoprotectants. Attention to the principles of osmosis were essential to inducing tolerance to cryoprotectant addition to organs. Yet despite efforts to control deleterious osmotic effects of cryoprotectants, limits of tolerance to cryoprotectants are still observed. There appear to be genuine, inherent toxic effects of cryoprotectants that are independent of the transient osmotic effects of these chemical agents.

Studies by the present inventors and others have examined methods of controlling the non-osmotic, inherent toxicity of cryoprotective agents. The results indicate that several techniques can be effective alone and in combination. These include (a) exposure to the highest concentrations at reduced temperatures; (b) the use of specific combinations of cryoprotectants whose effects cancel each other's toxicities; (c) exposure to cryoprotectants in carrier solutions that are optimized for those particular cryoprotectants; (d) the use of non-penetrating agents that can substitute for a portion of the penetrating agent otherwise needed, thus sparing the cellular interior from exposure to additional intracellular agent; and (e) minimization of the time spent within the concentration range of rapid time-dependent toxicity. Means by which these principles could be applied to whole organs so as to permit them to be treated with vitrifiable solutions without perishing, however, have not been clear or available.

Some of these techniques are in potential conflict with the need to control osmotic forces. For example, reduced temperatures also reduce the influx and efflux rate of cryoprotectants, thereby prolonging and intensifying their osmotic effects. Similarly, minimizing exposure time to cryoprotectants maximizes their potential osmotic effects. Thus, there must be a balance reached between the control of osmotic damage and the control of toxicity. Adequate means for obtaining this balance have not been described in the literature. It is also true that, in some cases, intensifying osmotic effects of cryoprotectants by minimizing exposure times to these agents can be beneficial and complementary to the reduced toxicity that results, but safe means for achieving this in whole organs have not been described.

Organ preservation at cryogenic temperatures would permit wastage of valuable human organs to be considerably reduced and would facilitate better matching of donor and recipient, a factor which continues to be important despite the many recent advances in controlling rejection. See, Takiff, H., et al., Transplantation 47:102–105 (1989); Gilks, W. R., et al., Transplantation 43:669–674 (1987). A recent approach to the induction of tolerance to transplanted organs requires 10–200 days for the host immune system to be "re-educated" to accept the graft as "self", a time that can only be attained by being able to cryopreserve the cadaver organ See, Posselt, A. M., et al., Science 249:1293–1295 (1990); Remuzzi, G., et al., The Lancet 337:750–752 (1991).

One major limitation in organ cryopreservation studies has been the lack of suitable equipment for controlling perfusion parameters such as cryoprotectant concentration-time history, pressure, and temperature. Previously described standard perfusion machines are not designed for this application and are unable to meet the requirements addressed here. Patented techniques heretofore known are described in:

U.S. Pat. No. 3,753,865 to Belzer et al.
U.S. Pat. No. 3,772,153 to De Roissart et al.
U.S. Pat. No. 3,843,455 to Bier
U.S. Pat. No. 3,892,628 to Thorne, G. H., et al.
U.S. Pat. No. 3,914,954 to Doerig, R. K.
U.S. Pat. No. 3,995,444 to Clark et al.
U.S. Pat. No. 4,629,686 to Gruenberg, M. L.
U.S. Pat. No. 4,837,390 to Reneau, R. P.

Equipment described for cryopreservation applications in the past have permitted only relatively simple experimental protocols to be carried out, and have often been awkward to use. Only Adem and Harness have reported using a computer for organ perfusion with cryoprotectant See, Adem, C. G., et al., J. Biomed. Engineering 3:134–139, 1981. However, their specific design has several major flaws that limits its utility.

The present invention overcomes substantially all of the deficiencies of known apparatus and methods.

SUMMARY OF THE INVENTION

In its most basic form, the present invention is directed to a computer-controlled apparatus and method for perfusing a biological organ, such as a heart, kidney, liver, etc. The apparatus of the invention comprises a plurality of fluid reservoirs and an organ container for holding the biological organ. A first fluid flow path is defined as a loop from the plurality of reservoirs to necessary sensors and temperature conditioning means and back to the plurality of reservoirs. The reservoirs are selectively connectable to the first fluid flow path. Pump means are interposed in the first fluid flow path for pumping fluid from the first fluid flow path to a second fluid flow path. The organ container is located in this second fluid flow path. Pump means may also be included in the second fluid flow path for pumping fluid from the organ container to one or more of the reservoirs or to waste. One or more sensors are interposed in the fluid flow paths for sensing at least one of the concentration, temperature, pH, and pressure of the fluid flowing in the first and second fluid flow paths. Measuring means are interposed in the first and second fluid flow paths for measuring concentration and temperature differences between the upstream and downstream sides, in the fluid flow direction, of the organ container. The sensor(s) and the measuring means are connected to a programmable computer for providing a continuous information stream from the sensor(s) to the computer. Finally, the computer is coupled to the selection means and the pump means to continuously selectively control (a) the flow of fluid from each of the reservoirs individually to the fluid flow paths, and (b) at least one of the concentration, temperature, pressure and pH of the fluid flowing in the second fluid flow path, in accordance with a predetermined computer program without operator intervention.

Additional features of the invention may include a heat exchanger interposed in the first fluid flow path for conditioning the temperature of fluid flowing from this fluid flow path. A second heat exchanger may be interposed in the second fluid flow path for conditioning the temperature of fluid flowing in the second fluid flow path. A third fluid flow path may be defined between the organ container and the plurality of reservoirs. A third pump may be interposed in the third fluid flow path for pumping fluid from the organ container to one or more of the reservoirs.

FEATURES AND ADVANTAGES OF THE INVENTION

This invention has a multitude of features and advantages, among the most important of which are:

1. It permits control of the concentration of cryoprotectant or any other fluid or drug in the perfusate of an organ according to a wide variety of predetermined concentration-time histories, more or less independently of the flow rate of perfusate through the organ, with provision for simultaneously varying the concentrations of other drugs or osmotic agents. Step changes in concentration are possible, and it is possible to bring concentrations effectively to zero.

2. It provides for in-line sensing of concentration, pH, perfusate temperature, and other parameters so as to avoid the need for sensors in the perfusate reservoirs and for manual measurements.

3. It permits minimizing differences between the concentration of cryoprotectant monitored and the concentration of cryoprotectant in the perfusate reservoirs by minimizing the time required for perfusate to travel from the reservoirs to the perfusate sensors and back to the reservoirs.

4. It permits minimizing differences between the concentration of cryoprotectant monitored and the concentration of cryoprotectant actually perfused into the organ by minimizing the time required for perfusate to travel from the main fluid circuit to the perfused organ (or superfused tissue).

5. It permits monitoring of the arterio-venous difference in cryoprotectant concentration across the organ as an index of the degree of, or opportunity for, organ equilibration with cryoprotectant.

6. It permits control of the temperature of the organ essentially independently of flow through the organ, and permits varying this temperature at will.

7. It permits control of the perfusion pressure, either keeping it fixed or changing it as desired, and if desired minimizing pulsation.

8. It protects against perfusion of unmixed solution and air (bubbles) into the organ.

9. It interface with a computer to control the perfusions, to provide real-time monitoring, display, processing, and recording of the data, to calibrate the sensors and pumps, and to direct the cleaning, disinfection, and priming of the perfusion circuit and to instruct and alert the operator when necessary.

10. It is capable of perfusing and cryoprotecting organs of widely varying size, e.g., anything from a rat heart to a human liver, and is capable of tissue superfusion as well.

BRIEF DESCRIPTION OF THE DRAWING

FIGS. 6A–E comprise a flow chart of activities for organ cryoprotectant perfusion.

FIGS. 7A–B comprise a flow chart of the procedure for non-cryoprotectant perfusions.

FIG. 8 shows the function (control of serum creatinine) of rabbit kidneys transplanted after perfusion with VS4.

DETAILED DESCRIPTION OF THE PREFERRED EMBODIMENT AND BEST MODE

Figure 1:
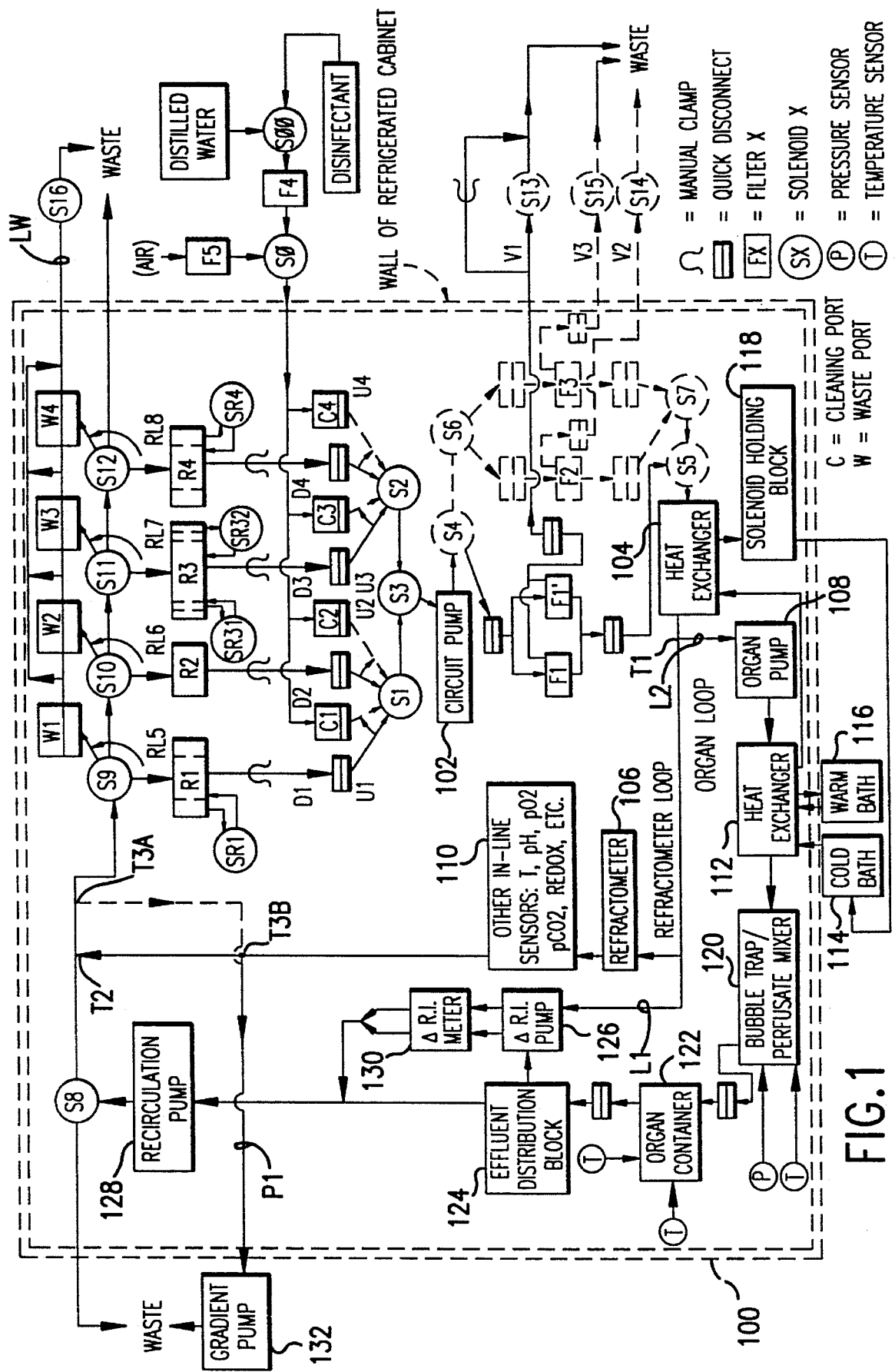
FIG. 1 shows the overall fluidic circuit diagram of this invention.

In a preferred embodiment, the apparatus incorporating the principles and features of this invention is contained in a refrigerated cabinet 100 (shown by double dashed lines in FIG. 1). The refrigerated cabinet contains two sides, the reservoir/solenoid side and the organ/refractometer side. The cabinet is faced with double paned transparent doors each containing approximately 1 inch of insulating air (which can be reduced in pressure and/or humidity if necessary) between the panes to avoid condensation of moisture on the doors and to minimize heat leak to the cabinet. The organ-side door is split to form a "Dutch door". This allows the upper portion of the organ-side door to be opened and closed to place the organ in the system and to remove the organ without changing the temperature below the upper portion of the door, where the organ container and most other equipment is located. The cabinet may also employ a "Dutch door" on the reservoir side of the cabinet to enable the operator to make any needed adjustments (e.g., fluid addition to the reservoirs, transfer of upper fluid lines, etc.) without disturbing cabinet temperature to an unnecessary degree.

The primary features of the invention and its mode of operation are shown in the fluidic logic schematic of FIG. 1. All fluid available for circulation through the system is drawn into the main circuit by a circuit pump 102 through fluid uptake lines U1, U2, U3, or U4 depending upon the computer-controlled actuation pattern of three-my solenoid valves S1, S2, and S3. Uptake lines U1–U4 connect either to fluid delivery lines D1–D4 leading from reservoirs R1–R4, respectively, or to cleaning ports C1–C4, through standard tubing quick disconnects. By clamping D1–D4 and unplugging them from uptake lines U1–U4, lines U1–U4 can be plugged into cleaning ports C1–C4, as indicated by the curved arrows. While this is presently done manually, it will be appreciated by those skilled in the relevant arts that appropriate valves, tubing and controls could be added to handle this task automatically.

In the embodiment of the invention as presently constructed, the reservoirs R1–R4 are supported on a thick transparent plastic shelf from which four magnetic stir tables hang which stir the four reservoirs. Thorough stirring of R1, R3, and R4 is necessary for proper generation of the desired concentration-time histories. The on/off states and stir rates of the stir tables are independently controlled.

Ports C1–C4 lead to sources of sterile (distilled) water, air, and disinfectant. Solenoid valves S0 and S00 are interposed in the delivery lines for these sources and are arranged to ensure that traces of disinfectant do not enter the perfusion system by accident. Solenoid S0 controls whether air or fluid will enter the perfusion circuit for cleaning, while solenoid S00 determines whether the fluid selected will be water or disinfectant. The breakup of the main cleaning line into four independent channels outside of the cabinet rather than just before reaching C1–C4 ensures that each channel is independent of the others, i.e., not subject to any meaningful cross-contamination resulting from diffusion of unpurged solution backwards from the fluid uptake lines U1–U4 into the cleaning lines leading to cleaning ports C1–C4.

Distilled water and disinfectant are drawn into the system through a sterilizing filter F4, while air is drawn into the system through an air filter F5. The disinfectant of choice at present is a clinically accepted dialysis machine cold sterilant such as Actril. The cleaning procedure is to wash the perfusate out of the system with water and then to displace the water with sterilant. Prior to the next perfusion, the sterilant is washed out of the system with water and the water is then washed out of the system with air. The system is then primed by displacing the air with appropriate perfusate. The air flush is used to avoid the persistence of any lingering traces of sterilant dissolved in the rinse water, and to avoid any possible dilution of the priming fluid with water (i.e., to reduce the amount of priming fluid needed for displacing water from the system), to allow a visual check of the completeness of priming, and to reduce spillage of water in the cabinet when the reservoirs, filters, and organ cassette are placed into the system after cleaning but before priming. The air purge can, however, be omitted if desired. The air filter is used to prevent contamination from pathogens in the air, if neccessary.

Solenoid valves S9–S12 normally direct fluid to reservoirs R1–R4 or to waste. Reservoirs R1–R4 can also be detached from the system by removing recirculation lines RL5–RL8 from reservoirs R1–R4 and plugging them into waste ports W1–W4, respectively (as indicated by curved arrows), allowing reservoirs R1–R4 to be removed from the system for cleaning, sterilizing, and refilling. When reservoirs R1–R4 are removed, valves S9–S12 direct fluid to waste ports W1–W4. The four waste lines corresponding to waste ports W1–W4 converge to a single common waste line LW. A two-way solenoid valve S16 is located on the common waste line. When the waste ports are not in use, the common waste drainage line is blocked by closing valve S16 to prevent any possible backflow of waste or pathogens into the sterile cabinet.

The use of this system of uptake lines U1–U4, which are plugged alternately into reservoir delivery lines D1–D4 or cleaning ports C1–C4, in combination with recirculation lines RL5–RL8, which are plugged alternately into the reservoir internal return lines (not shown in the figure) or into waste ports W1–W4, allows complete sterilization of the perfusion circuit. The blunt ends of the uptake lines U1–U4, delivery lines D1–D4, cleaning ports C1–C4 and waste ports W1–W4 may be sterilized by swabbing with disinfectant when the tubing is being transferred from one alternative position to the other. The tubing transfer is accomplished while applying digital pressure to the tubing so as to occlude it while making the transfer to prevent fluid leaks and further reduce the risk of contamination.

The fluid withdrawn from reservoirs R1–R4 or from ports C1–C4 is delivered through one of several filters F1, F2, and F3, depending upon the state of actuation of solenoid valves S4 through S7. These actuation patterns will be described in more detail below. Experience has shown, however, that a single filter F1 or two filters F1, F1' in parallel will be adequate for most studies (rendering valves S4–S7 optional, as indicated by broken lines) since virtual step changes in concentration can be imposed even when only one filter or two filters in parallel are present in the circuit.

It is desirable to minimize the distance between the circuit pump 102 head and the solenoids S1–S7 to minimize circuit dead space and dead time and minimize the effects of perfusate viscosity.

The filters are capable of sterilizing the perfusate and are autoclavable. All filter holders can be removed from the system for cleaning and sterilization by means of the quick disconnects shown in FIG. 1. Vent lines V1–V3 lead to solenoid valves S13–S15, located outside of the refrigerated portion of the cabinet 100. These vent lines are opened and closed under computer control during priming and cleaning of the system to permit air to escape and thereby prevent the filters from becoming blocked or damaged. A manual bypass (shown only for the S13 bypass) is provided for V1–V3 for emergency purging of air from the circuit. Obviously, air purges of the system beyond filters F1–F3 are not possible if filters F1–F3 are present in the circuit; hence filters F1–F3 must be removed before beginning the washout of sterilant if an air purge is to be included in that procedure.

In the presently preferred embodiment, a 90 mm diameter filter of 0.22 micron pore size is located in each filter holder. This size filter is able to pass enough vitrification solution at 0° C. to permit the successful perfusion of a rabbit kidney, with an overlying 1.2 micron filter and a coarse prefilter to prevent clogging. The standard configuration for the operative version employs two identical filters in parallel. This is necessary to accommodate the flows required for human organs and provides a safety factor for any air which may be inadvertently introduced into the arterial fluid, as well as minimizing pressure building proximal to the filter. This continuous filter sterilization and resterilization of the perfusate during the perfusion can serve as a back up for pre-sterilized solutions in case of contamination for any reason during the perfusion.

Once the fluid from the selected reservoir has passed through the appropriate filter, it goes through some preliminary temperature conditioning in a heat exchanger 104 and then travels to a position as close to the organ as possible, at which point it encounters a "T" type tubing connector T1. The bulk of the flow passively takes the path L1 ("refractometer loop") that leads to a flow-through process control refractometer 106 that measures the index of refraction of the liquid and hence the cryoprotectant concentration. The remainder of the flow is directed through an organ loop L2 by means of an organ pump 108. The organ pump speed is controlled by the computer so as to maintain the desired organ perfusion pressure despite wide variations in the organ's vascular resistance. By changing the organ pump head and the diameter of the tubing going through it, a wide range of flows can be generated sufficient to perfuse organs of a wide range of sizes: organs as small as rat hearts and as large as human kidneys have been successfully perfused.

The flow rate delivered by the circuit pump 102, which supplies both the refractometer loop L1 and the organ loop L2, must be high enough to both exceed the flow rate through the organ at all times and to ensure that sufficient flow is available for the refractometer 106 and other in-line sensors, generally designated 110, for measuring temperature, pH, and other desired parameters of the perfusate to permit accurate measurements. The flow must also be high enough to minimize the "dead time" between changes in reservoir concentration and changes in the sensed concentration and other sensed parameters in the refractometer loop as well as to minimize the "dead time" between the reservoir and the organ. The circuit pump flow is limited by the need to prevent fluid from being delivered to the filters at a rate in excess of what these filters or the tubing leading to them can pass without failing, as well as by constraints of heat output and wear and tear on the circuit pump tubing. The speed of the circuit pump is usually not varied during an experiment and does not therefore usually require computer control, though computer control is available as an option.

After passing through the organ pump 108, the perfusate passes through a second heat exchanger 112 that finalizes perfusate temperature conditioning. This is done by adjusting the flow of both cold and warm liquid from cold and warm baths 114, 116, respectively, using computer-controlled pumps (not shown) between heat exchanger 112 and baths 114, 116.

The computer is able to vary flow through both the cold path and the warm path so as to adjust perfusate temperature in the arterial line and therefore also in the effluent of the organ. The arterial and effluent temperatures provide an indication of the actual organ temperature. By controlling the flow rate of cold and warm bath fluid, organ temperature can be adjusted independently of organ flow, provided flow is not close to zero. Experience has shown that arterial and venous temperatures at least as cold as –6° C. and at least as high as 25° C. can be achieved with this invention. Generalized cabinet cooling is not an alternative to the heat exchange system for subzero perfusions because cooling of the cabinets to subzero temperatures will cause freezing of the more dilute solutions in the tubing lines. Specific jacketing and cooling of the organ container is of theoretical value, however, and may optionally be included.

The temperature-conditioned perfusate is then debubbled and mixed in a bubble trap/mixer 120 just before entering an organ container 122. Arterial and venous temperature probes, generally designated "T" in FIG. 1, penetrate the wall of organ container 122 through simple holes. Pressure and, optionally, temperature is sensed in the bubble trap. Although shown separately in the drawing for ease of understanding, the bubble trap and mixer 120 are in fact an integral part of the heat exchanger 112, so heat exchange continues to be controlled while debubbling and mixing are accomplished. Experience has shown that mixing is important due to the tendency for layering of dilute solutions on more concentrated, denser solutions. Details as to the specific construction of the heat exchanger/bubble trap/mixer (HBM) are described below.

Under normal circumstances, the cooling fluid effluent from this second heat exchanger 112 is used to cool the perfusate passing through the preliminary heat exchanger 104. This cooling fluid then travels to a solenoid holding block 118 physically containing solenoids S1–S12, so as to draw off waste heat from these solenoids before returning to the cold bath.

The holding block 118 is equipped with an internal fluid path for drawing off waste heat from the solenoids and may be either metal or plastic. The solenoids are preferably 3–7 watt (or less) piston type 3-way solenoids of minimal internal fluid volume having orifices on the order of 0.156 inches or more and Cv values>0.16 or more (e.g., NR (Neptune Research) Model 648T033 fired with RC dropping circuits and 3-watt coils) while resisting pressures of up to 500 mmHg or so. Solenoids having 1/16 inch orifices and Cv values of 0.01 to 0.03 (e.g., Valcor's Model 20-2-3) are not fury satisfactory due to the high viscosity of the solutions used for cryopreservation (causing difficulty aspirating viscous fluid through S1–S3), the high flows desired for controlling dead times and for perfusing larger organs, the possibility of clogging, and the buildup of pressure between the circuit pump and S8–S12. The detailed actuation pattern and tubing arrangement of the solenoids is described below. The internal solenoids not held in the solenoid block, SR1, SR31 and SR32, are described in more detail below.

A stopcock (not shown) in one of the coolant lines permits the in-line heat exchanger to be bypassed if desired. When the cooling function of the solenoid holding block 118 is in use, the effluent is directed to the solenoid holding block cooling system before returning to the cold bath.

An effluent distribution block (EDB) 124 (FIG. 1) is connected to the output side of the organ container 122. The EDB is designed so that a small mount of effluent is always present at the bottom of the block. This effluent or residual fluid is withdrawn by the two-channel "delta R.I. pump" 126 and sent to the differential refractometer ("delta R.I. meter") 130 where its refractive index is compared to that of the arterial perfusate from refractometer loop L1 (pumped at the same rate as the venous effluent sample) and a difference signal generated. EDB 124 is drained also by the effluent recirculation pump 128. The EDB 124 therefore allows effluent to be recirculated with or without first being delivered by the delta R.I. pump 126 to a differential refractometer 130. The differential refractometer 130 sends a signal to the computer which provides a measurement of the difference in concentration between the fluid in the refractometer loop L1 and the organ effluent in the organ loop L2. The nonlinear baseline resulting from this unorthodox use of the differential refractometer is accounted for in the software for running the perfusion program. Since the fluid in the refractometer loop will approximate the concentration of the fluid entering the artery of the organ, the delta R.I. output provides an estimate of the arterio-venous concentration gradient across the organ. When this gradient is large (in either the positive or negative direction), the organ is far from equilibrium. When the gradient is zero, the organ is at least largely in osmotic equilibrium with the perfusate.

All effluent from the organ (together with the arterial fluid sampled by the delta R.I. pump) is ultimately collected by the recirculation pump 128 and sent to solenoid S8, which controls whether the effluent is recirculated to the reservoirs or discarded to waste. Effluent to be returned to a reservoir is combined with the fluid flowing through the refractometer loop L1 at a T connection T2. As noted above, return to the correct reservoir is then controlled by the actuation of solenoids S9 through S12.

The recirculation pump 128, like the circuit pump 102, need not require flow adjustment. It is normally set to a rate sufficient to exceed the maximum steady flow through the organ pump 108. Since the output of the recirculation pump exceeds that of the organ pump, air is continually introduced into the tubing leading to solenoid S8 and usually to the reservoirs R1–R4. Provisions to prevent excessive bubbling of the reservoirs as a result of this are described below.

Although the delta R.I. pump speed can be changed, it is usually kept constant throughout an experiment. In the presently operative version, it is not under computer control, but computer control would be a desirable option in some cases. The delta R.I. pump employs very small diameter tubing to reduce delays in fluid transit time. This small tubing is particularly important because the flow rate through the delta R.I. circuit is limited by the lowest flow rate through the organ, which may be small, and by the limited size of the fluid paths in commercially available differential refractometers.

The return of the differential refractometer output to the organ effluent line is proximal to the effluent recirculation pump. This placement rather than placement distal to the pump ensures a steady flow though the differential refractometer, whereas distal placement may prevent or alter differential refractometer flow by virtue of a higher exit pressure.

The present operative version of the embodiment of the invention uses silastic tubing of 1/8 inch diameter throughout the system, which is sufficient to accommodate the needed flows and is preferred. Silastic is compatible with Actril cold sterilant, is translucent (important for visualizing flow to detect problems and for observing any signs of microbial growth), is impervious to common cryoprotective agents such as dimethyl sulfoxide, and is soft enough to be easily manipulated. However, silastic should not be used in circuits coming into contact with silicone cooling fluids, which swell and weaken silastic tubing.

Figure 2A:
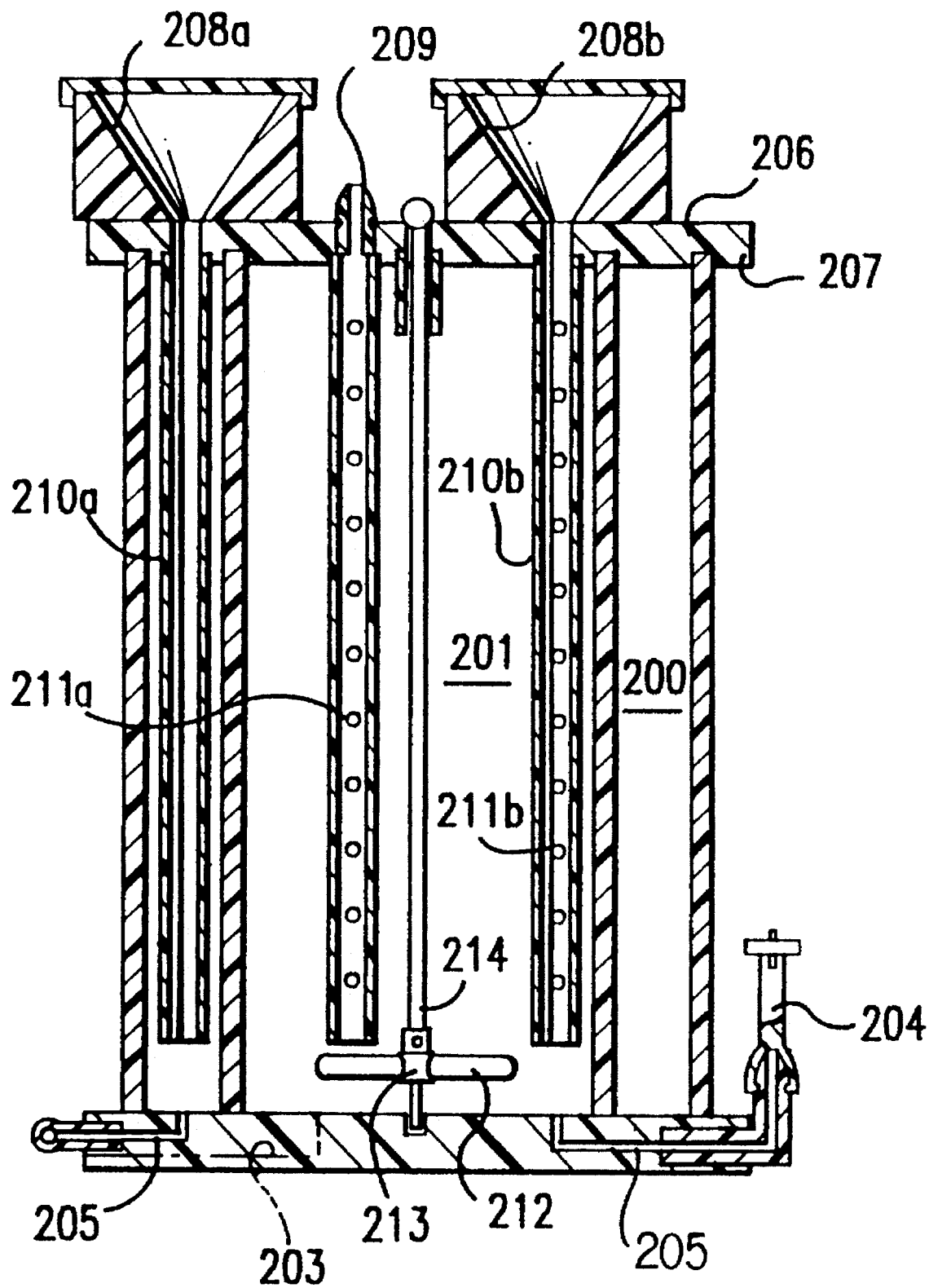
FIGS. 2A–C show side, top and bottom views, respectively of a two-chamber gradient former employed as reservoir R1 in this invention.
Figure 2B:
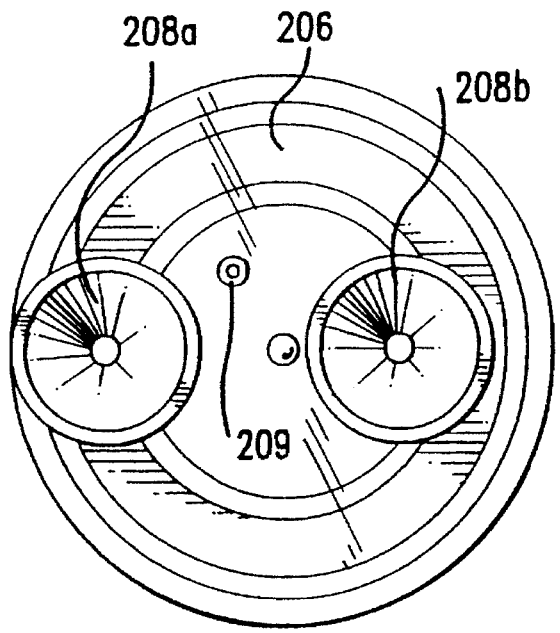
Figure 2C:
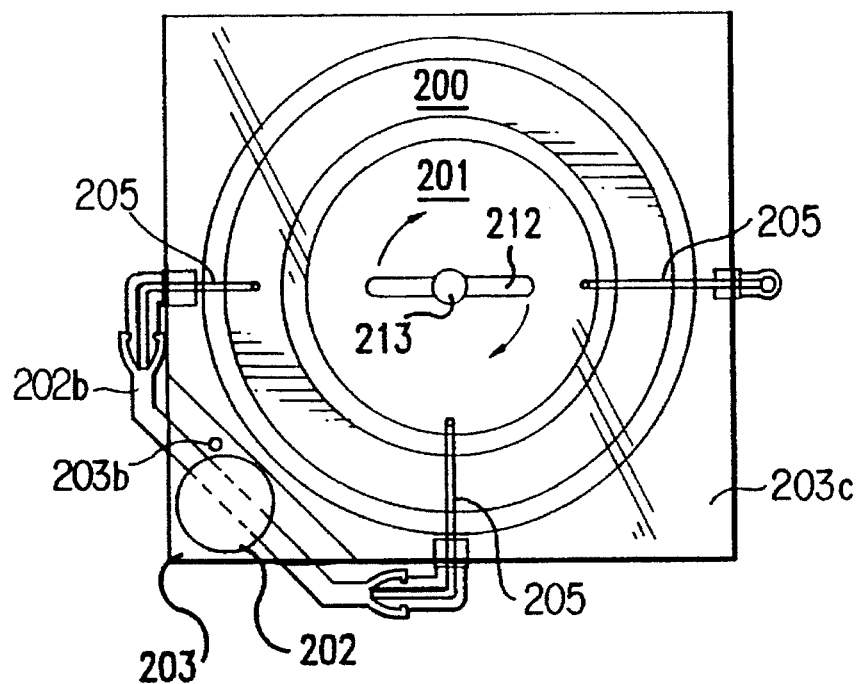

Reservoir R1 is constructed as a gradient former (FIG. 2). Essentially the gradient former consists of two concentric cylinders, an outer cylinder 200 and an inner cylinder 201. A fluid path 205 allows fluid to flow from the outer cylinder 200 to the inner cylinder 201 under the influence of gravity in response to a reduction of volume in the inner cylinder. The concentric orientation of the fluid compartments is very space efficient. The fluid delivery line 204 corresponds to the line D1 of FIG. 1. The unit shown is a modification of a commercially available gradient former. The necessary modifications for use with this invention are as follows.

1) The stopcock normally used to control flow from the outer cylinder to the inner cylinder in the commercial device is replaced by a pinch-type two-way (on/off) solenoid valve 202 (currently, a Bio-Chem Valve Corp. model 100P2WNC). The pinch-type valve is preferable for this application to a piston-type valve because of the small pressure difference available to drive fluid flow and the consequent need for a large working diameter fluid path. It is also preferable for easy removal from its robing when the reservoir is to be removed from the cabinet for cleaning, leaving the solenoid behind. The base of the gradient former has been modified, at 203, to make room for the solenoid and to support it on a platform so as to keep the solenoid oriented correctly. The solenoid is located a sufficient distance from the reservoir to avoid excessive heating of the reservoir fluids.

2) The diameter of the fluid path 205 from the outer cylinder 200 to the inner cylinder 201 has been enlarged to permit flow at an adequate rate of the viscous solutions required for organ cryopreservation. An inner diameter of 1/8 to 3/16 inch is adequate.

3) A lid 206 has been provided. The lid has an outer overhang 207 that prevents the lid from moving from side to side after it is placed on the cylinder. The lid has built-in outer and inner filling funnels 208a and 208b, and a recirculation port 209.

4) Funnels 208a and 208b extend into respective internal fill tubes 210a and 210b. The internal fill tubes are preferably rigid hollow rods located next to the wall of the inner and outer cylinders and perforated at 1–2 cm intervals with holes 211a and 211b, respectively, which are approximately 3 mm in diameter. The function of the fill tubes is to reduce the creation of bubbles as recirculating fluid impacts the surface of the liquid in the reservoir. The purpose of the perforations is to enable air to escape from the tube through the perforations so as not to force air to the bottom of the reservoir to form bubbles. These functions are particularly important in perfusates containing protein, which tend to stabilize bubbles.

5) A fill mark has been provided to enable the reservoir to be filled reproducibly to the same, predetermined volume. The operator can establish his/her own fill mark depending upon the details of the application. The gradient formers have approximate graduations (horizontal lines on both the inner and outer cylinders, aligned so as to permit avoidance of parallax error in reading the liquid level in either cylinder) spaced approximately 0.5 cm apart for a 2 liter gradient former. These graduations are also important for establishing slight, deliberate mismatches in liquid level between inner and outer cylinders, which are necessary to prevent premature mixing of solutions of widely differing densities, such as cryoprotectant-free perfusate and vitrification solution. They also permit a rough quantitative check by the operator on the progress of the gradient as represented on the computer screen.

6) The plastic composition of commercially available gradient formers may create problems for certain types of cryoprotectant, which could conceivably attack the plastic. It is therefore preferred to use reservoirs made of transparent material (e.g., glass, plexiglass or the like) that is compatible with the cryoprotectant chemicals or use reservoirs whose surfaces have been siliconized or otherwise treated to prevent the attack. In the inventors' experience, acrylic has been found to be an acceptable material.

7) The reservoir R1 contains a stir bar 212, The stir bar is housed in a jacket 213 attached to a freely spinning vertical pin 214 extending to the stir bar from the lid of the reservoir to prevent the jacket, and hence the stir bar, from moving laterally. This change is necessary to make sure chattering, and therefore poor mixing, does not occur while the perfusion machine is unattended. Support from above rather than below prevents unnecessary perfusate frictional heating and avoids drainage/cleaning problems.

Figure 3A:
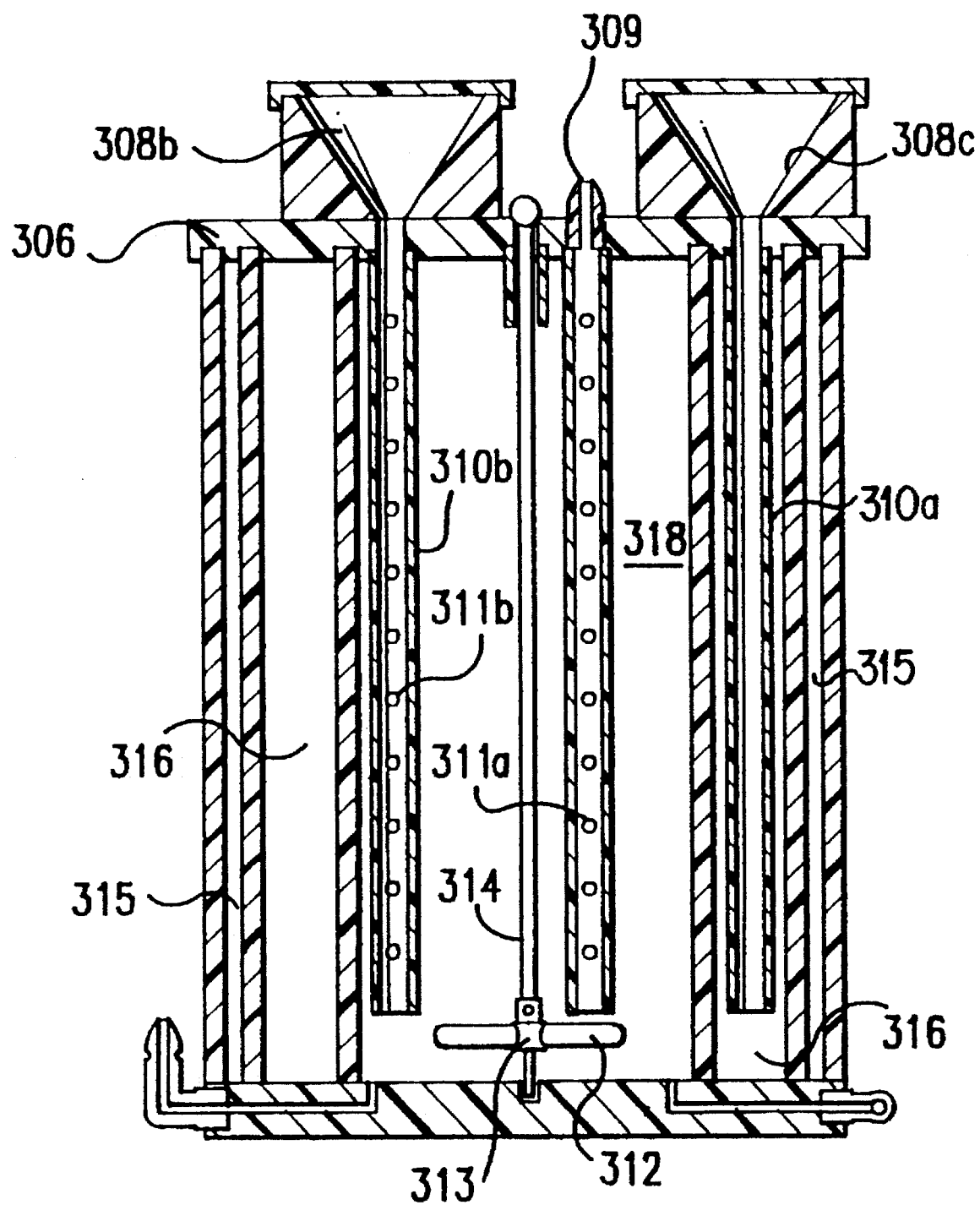
FIGS. 3A–C show side, top and bottom views, respectively, of a three-chamber gradient former used as reservoir R3 in this invention.
Figure 3B:
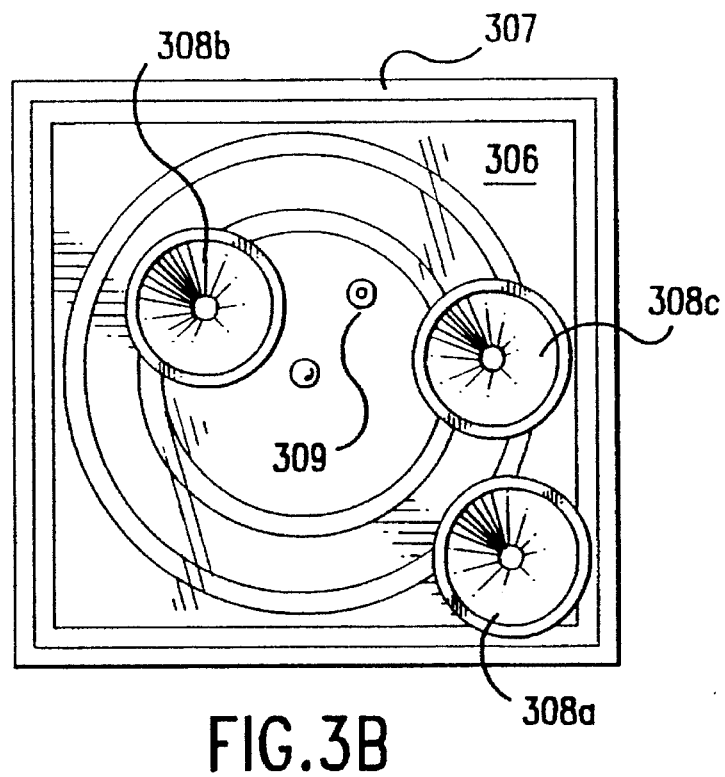
Figure 3C:
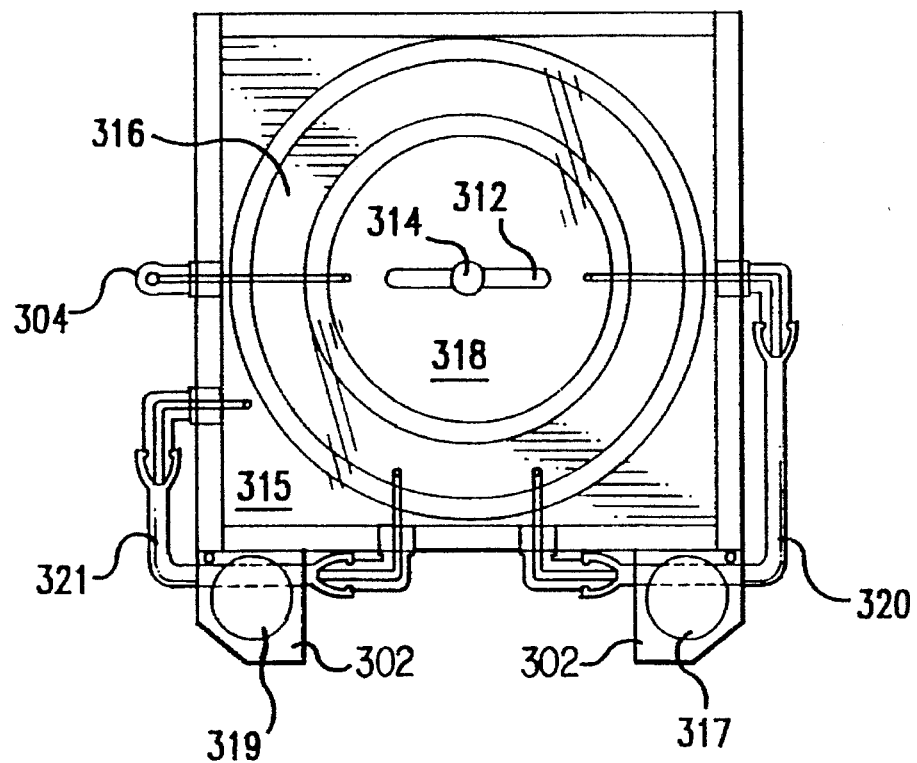

Reservoir R3 is also constructed as a gradient former. The details of reservoir R3 are shown in FIG. 3. In the drawing, those elements that are substantially the same as in reservoir R1 are designated with the same reference number, except that the first digit has been changed from a "2" to a "3". Reservoir R3 contains an outer compartment 315 ($R3_3$), an inner compartment 318 ($R3_1$), and a third intermediate compartment 316 ($R3_2$). Intermediate compartment 316 is connected to inner compartment 318 through a fluid conduit 320 controlled by a solenoid 317 ($SR3_1$). Compartment 316 also connects to outer compartment 315 by a fluid conduit 321 controlled by a solenoid 319 ($SR3_2$). The use of an outer compartment is necessary when concentration is being reduced to zero or nearly zero, for reasons noted below in the discussion of the function of the gradient pump and the action of the gradient formers. The outer compartment is necessary in preference to a larger volume of fluid in the middle compartment because increasing the volume of fluid in the middle compartment will cause the concentration profile of fluid flowing from the gradient former to waste in response to a constant efflux rate of inner cylinder fluid to become non-linear, therefore making control of concentration-time history more complicated. More importantly, an excessive amount of fluid in the middle compartment would be required to approach a zero concentration in the circuit compared to the amount of fluid required in the outer compartment after virtual emptying of the inner and middle compartments.

Automated use of reservoir R3 poses some problems which are successfully addressed in part by software and in part by the specific construction of R3. Specifically, actuation of solenoid-$SR3_2$ allows fluid in the outer compartment ($R3_3$) to flow first into the middle compartment ($R3_2$) and from this compartment to the inner cylinder ($R3_1$). This is because the pressure head present between $R3_3$ and $R3_2$ is large when $R3_1$ and $R3_2$ are nearly empty, which occurs when $SR3_2$ is activated. At this point, $R3_3$ is still full. This large pressure head causes fluid to flow too rapidly into $R3_1$ if $R3_3$ is connected directly to $R3_1$ rather than using $R3_2$ as a buffer between $R3_3$ and $R3_1$. By adjusting the level of $R3_3$, the flow can also be partially controlled. But even with these two precautions, further control of flow is required by using an appropriate duty cycle for $SR3_2$. The flow to $R3_1$ should be slow at first and more and more rapid as the concentration is brought closer and closer to zero, whereas passive flow under the influence of gravity will always be fastest at first and slowest at the end unless the flow is metered by the sort of tailored duty cycle currently being imposed on $SR3_2$.

The other modifications to R3 resemble those of R1.

Reservoir R4 is a gradient former constructed in the same manner as R1.

An important element of the fluidic circuit is the gradient pump 132 connected to the circuit by a line P1 (FIG. 1). The function of the gradient pump is to allow for gradual changes in concentration within the appropriate reservoirs within the cabinet. The method by which this is accomplished will be described below. The placement of the line P1 to the gradient pump at T3A, just after the point of joining of the refractometer loop L1 and the organ loop L2, presents one option for ensures removal of some of the air introduced by the organ effluent recirculation pump 128 and therefore helps reduce bubbling of the reservoir fluid.

A better option, however, and the one presently in use, is to draw no air into line P1. This is accomplished by connecting P1 at point T3B and results in fully controlled concentration-time histories. The bubbling problem is then overcome by continuously regulating the speed of the recirculation pump 128 to be just slightly in excess of the combined flows of the organ pump 108 and the delta R.I. pump 126 so as to introduce little air. Attaching the recirculation output of S8 directly to P1 without regulating the speed of pump 128 results in degraded concentration history and is not recommended.

The purpose of the gradient pump 132 is to remove some of the recirculating fluid from the circuit. This removal of fluid causes the flow rate of fluid back to the reservoir of origin to be less than the flow rate of fluid from this reservoir to the circuit. This causes the level in the inner cylinder of the reservoir (R1, R3, or R4) to go down. This lowering of inner cylinder fluid level in turn causes the fluid in the outer or middle compartments to flow into the inner cylinder to keep the two levels similar. Thus the two dissimilar concentrations in the two cylinders are mixed in the inner cylinder, generating the concentration gradient which is then sent to the rest of the circuit. This is the manner in which the gradient pump effects the desired gradual changes in concentration which reach the organ and the refractometers. Any necessary adjustments to the gradient pump speed are made by the computer.

The principle involved is that of an ordinary linear gradient former in which the portion of the circuit external to the gradient former can be regarded, to a first approximation, as extra volume in the inner cylinder. Withdrawal and discard of fluid from the inner cylinder at a constant rate will result in a linear molar concentration increase with time despite the presence of the rest of the circuit and the recirculation of fluid back to the reservoir. However, unlike an ordinary gradient former, the concentration of fluid leaving the gradient former at the moment the volume in the gradient former becomes zero will not be equal to the concentration of fluid in the outer (or middle) cylinder of the gradient former. Therefore, in order to approach a concentration of zero during cryoprotectant washout using an ordinary two-compartment gradient former, it is necessary to add additional fluid to the outer cylinder while continuing to discard fluid from the inner cylinder normally. This is why R3 has been modified to have a third compartment: the extra fluid required to continue cryoprotectant washout can be added from this third compartment by the computer without operator intervention which could compromise temperature control and introduce inaccuracies. During introduction of cryoprotectant, on the other hand, the desired final concentration can always be reached by using a concentration in the outer compartment which significantly exceeds the final concentration desired in the circuit at the end of the gradient The HBM heat exchange system is shown in detail in FIGS. 4A–E.

Perfusate enters the HBM through an entry port 403, travels through a central channel 400, and leaves the HBM via an outlet port 406. On either side of the central perfusate path are separate chambers for regulating temperature. The two innermost temperature control chambers 401 (one on each side of the perfusate path) are used for the circulation of coolant, while the outer chambers 402 are a pathway for the flow of room temperature fluid for offsetting the coolant. (For specialized applications involving, for example, normothermic perfusion, these pathways can be reversed.)

The direction of cold fluid flow is optional. Adequate temperature control has been found when all fluids (perfusate, coolant, and warming fluid) flow in the same direction (uphill) despite the lack of countercurrent heat exchange. This mode allows the avoidance of air or carbon dioxide accumulation in the outer chambers.

Perfusate enters the bottom of the HBM unit through inlet 403 and travels upward in a zig zag pattern. It emerges into a small upper reservoir which has an air space above: this is the bubble trap area 404. Perfusate then travels beneath the bubble trap and goes through a perfusate mixing area 405 before finally traveling onward to the arterial outlet.

The inlets for cold 407 and warm 408 fluid are each split into two channels within the base of the unit. The outlets 410, 411 for warm and cold fluid, respectively, each receive fluid collected from two channels such that each channel of the same kind (i.e., each cold channel or each warm channel) is the same length and nominally experiences the same pressure difference from start to finish, so that flow rate through each like channel should be approximately equal.

All of the cold and warm fluid pathways include a length of flexible tubing 412 at the rear of the unit. These tubing segments serve two purposes. First, by introducing an air gap between the four channels, heat exchange between them is minimized. This is particularly desirable when all of the cold and warm fluid is flowing in the direction opposite to that of perfusate flow (i.e., in orthograde direction) and has not already undergone heat exchange with the perfusate. Second, each tube can be clamped. In this way, if by chance one cold channel or one warm channel should take all of the cold or warm fluid delivered while the other channel "airlocks"; this situation can be corrected by clamping the channel receiving all of the flow and purging the air out of the inactive channel, bringing each channel into full function and equal flow.

Because in orthograde mode the temperature conditioning fluid enters the heat exchanging portion of the unit at the top and exits at the bottom, it is necessary upon installation to run the cold and hot pumps in retrograde direction in order to purge all air out of the cold and warm channels. This is best accomplished if the cold and warm tubing leading to and from the bath is no more than about ⅛ inch in internal diameter, since at this diameter fluid flow will displace air from the tubing rather than allowing it to flow uphill in a direction opposite to the direction of fluid flow or otherwise to remain unpurged in various parts of the tubing. Thus, when the pump direction is reversed again from retrograde to orthograde, no air will be present in the tubing and none will be trapped in the heat exchange chambers of the unit.

In addition to serving a heat exchange function, the zig zag pattern is also designed to force mixing of previously perfused dense perfusate or, when perfusate density is rising rather than falling, to purge the less dense perfusate from the perfusate path.

As the perfusate emerges from the zig zag heat exchange area, it enters the bubble trap 404 at trap entry area 418. Perfusate exits the bubble trap through exit region 419. The zig zag pattern, in fact, is also designed to allow any air bubbles to exit the heat exchange area and to emerge into the bubble trap area. The bubble trap area is designed to have the following features:

1. Its volume is sufficiently large to reduce the pulsatile action of the perfusion pump to a minimum by distributing the shock of each stroke over a relatively large air volume. This simplifies pressure control and measurement and may be less damaging to the organ.

2. Its volume is sufficiently low to minimize the liquid volume present in the trap and thereby to minimize the dead time and dead volume between the organ pump and the organ itself. A minimal volume is also desirable to minimize layering of more dilute perfusate over more dense perfusate.

3. A pressure sensing port 413 is provided. Port 413 has no fluid connection to the perfusate, thus eliminating a "blind alley" in which fluid cannot be mixed properly or in which disinfectant might fail to penetrate or might be trapped.

4. The lid 414 of the trap is removable for cleaning.

5. A vent port 416 is provided which is used to adjust fluid level in the trap so as to make it the minimum required to serve the bubble trap function and to maximize pressure wave damping. The tubing from this vent leads to the outside of the cabinet, permitting adjustments to be made without opening the cabinet door. The same port leads to the electronic pressure transducer as well.

6. A third port 417 is provided through the bubble trap lid to permit the injection of drugs, vascular labeling materials, fixative, etc.

7. The walls of the bubble trap are angled near the trap entry and exit points 418, 419, respectively, to produce a certain amount of mixing of the perfusate both as it enters and as it leaves the trap, and to break up and minimize the volume of layers of dilute perfusate overlying more dense perfusate.

8. The option exists of introducing probes, such as a temperature probe via one of the ports in the trap lid to make measurements in the perfusate without permanent embedding of the sensor: the port consists of flexible tubing attached to a plastic threaded fitting. A probe can be freely admitted or withdrawn and the tubing clamped with hemostats or an equivalent clamp to effect a pressure-tight seal. This simplifies removal and reinstallation of the HBM when it must be cleaned and allows flexibility in probe selection and the opportunity of using the probe for other measurements elsewhere.

Figure 4A:
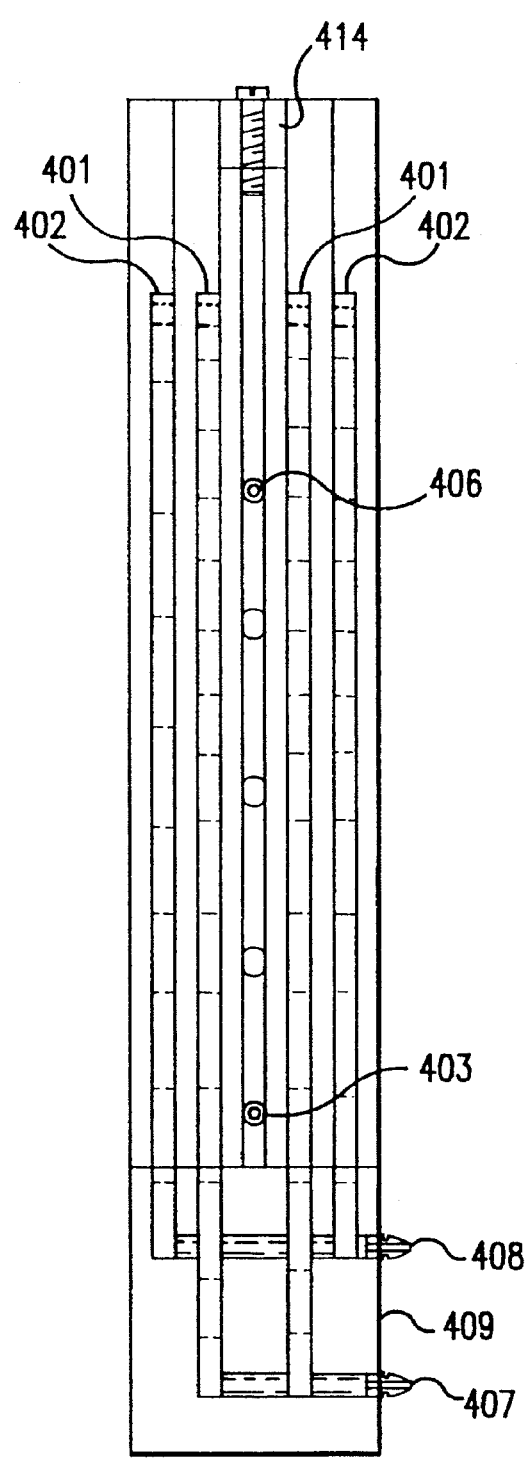
FIGS. 4A–C show front, side and rear views, respectively, of the HBM used in this invention.
Figure 4B:
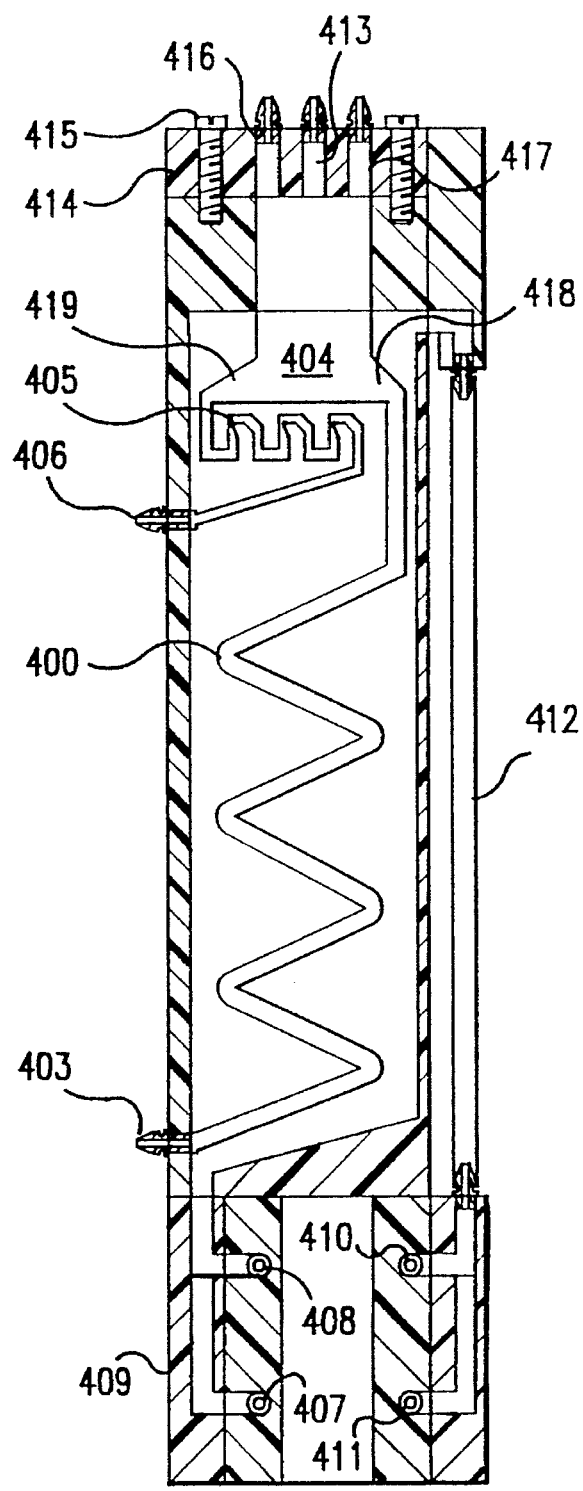
Figure 4C:
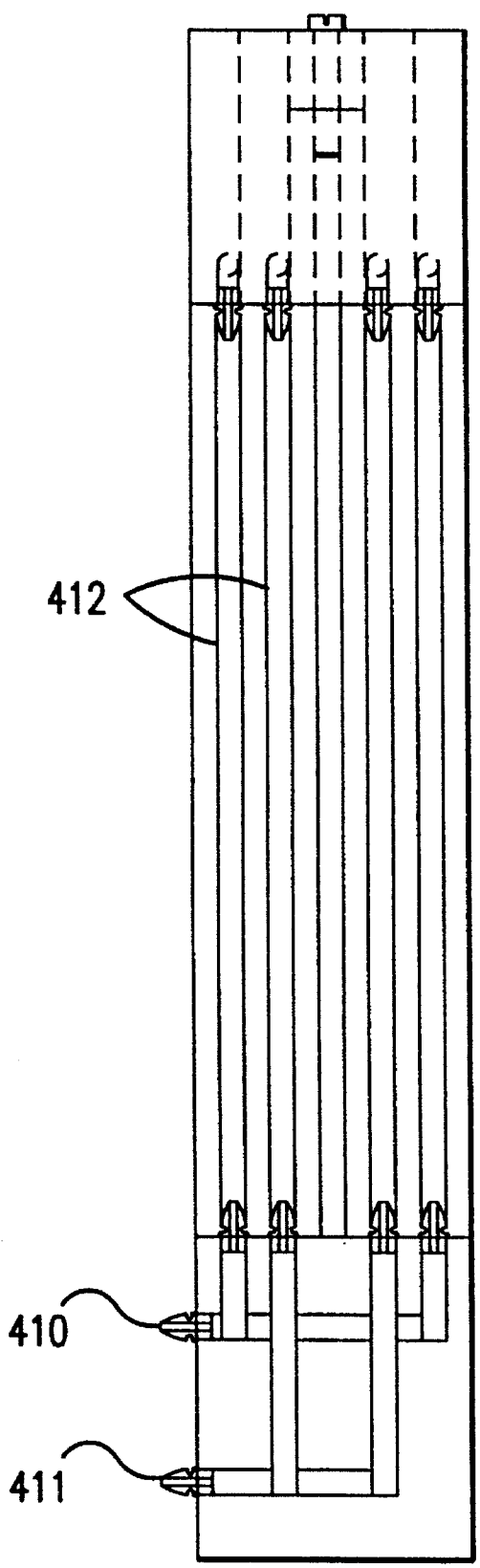
Figure 4D:
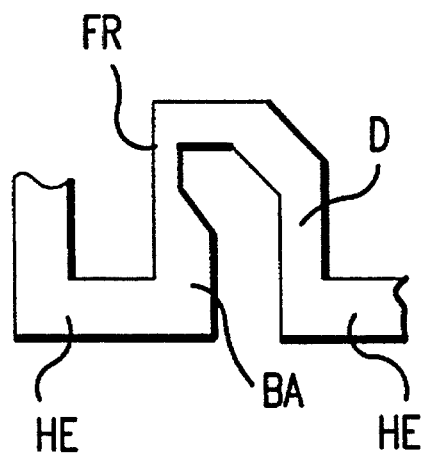
FIG. 4D shows the basic mixing unit area of the HBM.
Figure 4E:
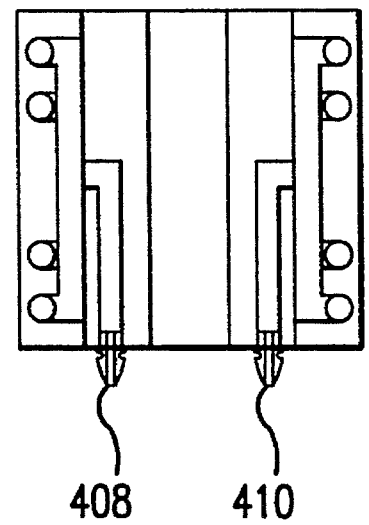
FIG. 4E shows a top view of the base of the HBM.

After leaving the bubble trap, the perfusate descends to a mixing area 405 (see FIG. 4D). The basic unit of the 3-unit mixing path is a narrow horizontal entry area HE emerging into a "wide" basal area BA which rises to an area of flow restriction FR and ends in a descent D to the next horizontal entry area. Fluid entering HE is forced through an opening too small to support much layering of low density fluid on top of high density fluid, especially considering the tight angle turn required just before HE. Fluid flowing into BA may, if less dense, rise immediately upward toward FR. If more dense, it may be driven into the wall W and rise upward along this wall. Upon encountering FR, however, the denser liquid will be accelerated toward the less dense liquid rising directly from HE, creating turbulence and mixing. If BA fills with dense perfusate, the speed of the fluid emerging at FR directly upwards toward D should cause the dense liquid to mix with any low density fluid layered above FR. Furthermore, the narrow descending path D should draw layered liquid down the angle along with denser liquid, again preventing stagnant layers from persisting. In practice, three such mixing units aligned in series as shown in FIG. 4B are sufficient to mix initially very poorly mixed perfusate, which is encountered frequently in the course of abruptly raising or lowering cryoprotectant concentration. One final function of the mixing units is to serve as a trap for any small bubbles which for any reason are not removed in the bubble trap area. (Bubbles in the mixing area are, however, easily purged by the operator prior to initiation of organ perfusion.)

After leaving the mixing region, the perfusate descends to an outlet port 406 leading directly to the organ. The path from the final mixing unit to port 406 is deliberately created at an angle to the horizontal in order to provide one last chance of stopping any bubbles from reaching the organ, since in order to reach the organ a bubble in this pathway would have to flow downhill, contrary to its tendency to flow uphill.

The mixing area and subsequent areas are purged of air by occluding the outlet tubing affixed to port 406 with the vent open until approximately ½ inch of fluid has accumulated in the bubble trap. The vent is then closed until the pressure has reached about 60–120 mmHg. Finally fluid is once again allowed to flow freely through port 406. The jet of fluid through the mixing area and out port 406 sweeps all air out of the fluid path from the bubble trap to port 406. If some air persists, it can be removed by repeating the process. After air has been purged, the vent is opened to allow unnecessary fluid in the bubble trap to exit the trap under the influence of gravity, reaching a final depth of about ⅛ inch. A final depth of ⅛ inch cannot be set before purging the line of air because insufficient volume exists to avoid refilling the mixing area with air from the bubble trap during the purging process.

The HBM is designed to require removal for cleaning only infrequently. Disinfection and removal of disinfectant from the bubble trap area is effected automatically but does require some operator attention afterwards to ensure that all uppermost exposed surfaces are disinfected and later washed free of disinfectant without contaminating the outlet tubes.

After the perfusate exits the HBM unit through port 406, it enters the organ in the organ container 122. In the preferred embodiment, the organ container comprises a rectangular box with a hinged lid, lid stop, lid handle, sloped floor, specially sloped feet, arterial and venous thermocouple inlets, perfusate inlet, and effluent outlet in the foot opposite the inlet. The slope of the floor is downward in both the right to left and the back to front directions to ensure that all fluid runs to the foot outlet with very little fluid accumulation anywhere in the container. One needle probe is inserted directly through the wall of the arterial line. A second probe is placed directly in the stream of fluid emerging from the organ. In typical results, the arterial and venous temperatures differ by only tenths of a degree, but both are useful for quality control. The organ container may employ a soft mesh support for the organ similar to that used in the Waters organ cassette or the organ can be placed directly on the floor of the organ container or on a specially designed independent and removable support.

The organ container 122 and the organ pump 108 are placed in maximum proximity to reduce dead times and dead volumes between the two, and the tubing leading from the organ pump to the organ container is chosen to be as small in inner diameter as possible for the same reason.

Most perfusate does not go through the organ loop L2 as described above but travels instead from the filters to the in-line analogue refractometer 106. The presently preferred embodiment of the invention uses a modified commercially available refractometer from Anacon corporation. In particular, small diameter tubing inlet and outlets are used rather than the very large standard Anacon pipe fittings.

The modification of the refractometer sensing head appropriate for the final invention could contain the following changes from the ordinarily available Anacon unit.

1. The internal volume of the fluid path could be kept to a minimum.

2. Presently, it is necessary to purge the air space of the unit with a slow flow of dry nitrogen gas to prevent condensation of moisture due to the low temperatures and high humidities prevailing in the cabinet. In a modified version, the electronics area of the sensing device could be hermetically sealed with some desiccant inside to eliminate the need for a nitrogen purge.

The invention allows the operator to access reservoirs in any sequence and to otherwise custom-design the process which may be of interest. The operator is even free to switch solenoid positions depending on what he may want to do. Nevertheless, the following nominal application illustrates the actuation patterns required to deliver fluid from and to each individual reservoir and filter. It also illustrates the "standard protocols" for organ cryoprotectant perfusion and for cleaning of the system which the system was designed primarily to carry out.

Solenoid S1 admits fluid from R1 when off, or from R2 when activated. Solenoid S2 is open to R3 when not energized, or to R4 when energized. The output of S1 and S2 is to S3, which accepts fluid from S1 (that is, from R1 or R2) when in the resting state and which accepts fluid from S2 (i.e., from R3 or R4) when activated. The common outlet for S3 (always open) leads to the circuit pump 102, which then withdraws fluid from the solenoid-selected reservoir.

If differential filters are to be included, then the output of the circuit pump 102 is to S4's common port (always open). When S4 is not energized, its output is directed to filter F1. The return from filter F1 returns to the normally open port of S5 and exits through the S5 common outlet to the refractometer loop L1 and the organ loop L2. If, on the other hand, S4 is energized, then its output is directed to the common inlet port of S6. When S6 is in the resting state, its output is directed to filter F2, and the return from filter F2 enters S7 through its normally open port. The output from S7 travels to the normally closed port of S5, which must be energized to accept this output. Once fluid has entered S5, it flows out the S5 common outlet to the refractometer loop and the organ loop. Finally if S4 is energized and S6 is also energized, fluid will be directed through both of these valves and will reach filter F3. The return from filter F3 occurs via the energized S7 and the energized S5 solenoids and goes to the two loops L1 and L2 as above. As noted earlier, the use of filters F2 and F3 and therefore of solenoids S4, S5, S6, and S7 is optional and will be useful primarily when very abrupt changes from one solution to another are required, or when particularly heavy particulate contaminates must be removed.

Effluent from the organ eventually returns to S8. If S8 is activated, the fluid is discarded. If S8 is not activated, the fluid is directed from S8 to combine with fluid from the refractometer loop and returned to a desired reservoir.

Fluid traveling through the refractometer loop travels successively to solenoids S9 S10, S11, and S12 and then to waste if none of these solenoids are energized. Energizing S9 diverts flow to the R1 recirculation line. S10's activation (in the absence of activation of S9) diverts flow to R2. Similarly, selective activation of S11 or S12 will, respectively, recirculate fluid to R3 or R4.

There are two basic processes of solenoid-actuated fluid control, one for actual perfusions and one for system cleaning and priming. The perfusion process typically proceeds from R1 through R4 whereas priming must occur in the reverse order to load the fluid uptake and fluid recirculation lines for reservoirs R2–R4 and, optionally filters F2 and F3 and their associated lines) while leaving the circuit primed with fluid from (typically) R1 (or C1) at the end of the priming (or cleaning) process. The typical sequence of solenoid activations required to prime the system (or to clean it) is as follows.

When only F1 (not F2) is present, priming (and cleaning) may proceed in any order of reservoirs, provided, in the case of priming, that the final reservoir corresponds to the first reservoir used for the subsequent perfusion.

SOLENOID CONTROL SEQUENCE for STANDARDIZED RINSING/PRIMING
(Uses: remove perfusate with filter-sterilized H₂O at end of experiment; replace cleaning H₂O with chemical sterilant solvent between perfusions; remove disinfectant using filter-sterilized distilled H₂O; remove water using air; remove air using reservoir fluid, i.e., prime the system.)

| | | SOLENOID # (+ = ENERGIZED) | | | | | | | | | | | | |
|---|---|---|---|---|---|---|---|---|---|---|---|---|---|---|
| | Sub-Task Accomplished | 00*0* | 1 | 2 | 3 | 4 | 5 | 6 | 7 | 8 | 9 | 10 | 11 | 12 | 13 |
| 1. | Deliver fluid from R4 through F1 | − | + | + | − | − | − | − | − | − | − | − | − | − | ** |
| 2. | Perfuse R4 recirculation tubing | − | + | + | − | − | − | − | − | − | − | − | − | + | − |
| 3. | Deliver from R3 through F3 | − | − | + | + | + | + | + | − | − | − | − | − | − | ** |
| 4. | Perfuse R3 recirculation tubing | − | − | + | + | + | + | + | − | − | − | + | − | − | − |
| 5. | R2, F2 | + | − | − | + | + | − | − | − | − | − | − | − | − | ** |
| 6. | R2 recirculation tubing | + | − | − | + | + | − | − | − | − | − | + | − | − | − |
| 7. | R1, F1 | − | − | − | − | − | − | − | − | − | − | − | − | − | ** |
| 8. | R1 recirculation tubing | − | − | − | − | − | − | − | − | − | + | − | − | − | − |
| 9. | Organ loop discard tubing*** | − | − | − | − | − | − | − | + | + | − | − | − | − | − |

*If the sequence above is to be done with reservoir fluid, S0 and SS00 will be off. S0 and S00 will also be off if the sequence above is to be done with water, and the cleaning ports C1–C4 will be connected to uptake lines U1–U4. If the sequence above is to be done with disinfectant, S0 will be off and S00 will be on. If the sequence is to be done with air, S0 will be on and S00 will be off.
S13 (and, optionally, S14 and S15), the filter vent solenoid(s), will be on for a portion of this step and off for the remainder of this step: it will be on just long enough to purge air from the line (usually 60 sec. on step 1 and 30 sec on each of the remaining steps for which the  notation is used). This can be programmed not to happen if the filters are not present in the system.
***this step is omitted when priming the system.
Note: Water control solenoid S16 is on (waste tube open for disposal of fluid to waste) for steps 2, 4, 6, 8, and 9 and off for all other steps.

The standard process of solenoid actuation for withdrawing fluid from R1–R4 and for creating gradients for a normal perfusion is as follows (assuming (1) use of optional filters F2 and F3, (2) straightforward or typical use of the gradient-controlling solenoids, and (3) the existence of a gradient former as R2). The staged completion of a closed circuit upon going from one reservoir to another is to avoid recirculating solution of undesired composition to the new reservoir before its contents have displaced the previous solution from the circuit. If there is no problem with recirculating the previous solution, the precaution of delayed recirculation can be dropped.

| SOLENOID CONTROL SEQUENCE for STANDARDIZED PERFUSION | | | | | | | | | | | | | |
|---|---|---|---|---|---|---|---|---|---|---|---|---|---|
| | | SOLENOID # (+ = ENERGIZED) | | | | | | | | | | | |
| Sub-Task Accomplished | 00*0* | 1 | 2 | 3 | 4 | 5 | 6 | 7 | 8 | 9 | 10 | 11 | 12 |
| 1. Initial recirculation to R1 | − | − | − | − | − | − | − | − | − | + | − | − | − |
| 2. R1 gradient | Same as 1, but activate SR1 | | | | | | | | | | | | |
| 3. From R2 to F1, no recirculation | + | − | − | − | − | − | − | − | + | − | − | − | − |
| 4. Deliver R2 solution through F2, no recirculation | + | − | − | + | + | − | − | + | − | − | − | − | |
| 5. Recirculate R2 solution except from organ | + | − | − | + | + | − | − | + | − | + | − | − | |
| 6. Recirculate all R2 solution | + | − | − | + | + | − | − | − | − | + | − | − | |
| 7. Run a gradient from reservoir R2 | Same as 6, but activate SR2 | | | | | | | | | | | | |
| 8. Perfuse from R3 just to S6/F2** | − | − | + | + | + | − | − | + | − | − | − | − | |
| 9. Perfuse from R3 to F3, circuit open | − | − | + | + | + | + | + | + | − | − | − | − | |
| 10. Recirculate to R3 except from organ | − | − | + | + | + | + | + | + | − | − | + | − | |
| 11. Recirculate all R3 fluid | − | − | + | + | + | + | + | − | − | − | + | − | |
| 12. Run first part of R3 gradient*** | Same as 11, but activate SR31 | | | | | | | | | | | | |
| 13. Run second part R3 gradient | Same as 11, plus SR31 and SR32 | | | | | | | | | | | | |
| 14. Open circuit, perfuse from R4 through F3 | − | + | + | + | + | + | + | + | − | − | − | − | |
| 15. Recirculate to R4 except from organ | − | + | + | + | + | + | + | + | − | − | − | + | |
| 16. Recirculate from both loops to R4 | − | + | + | + | + | + | + | − | − | − | − | + | |
| 17. Run R4 gradient | Same as 16, but activate SR4 | | | | | | | | | | | | |

*For normal perfusions, solenoids S0, S00, and S13–S16 will always be non-actuated.
**This step prevents fluid from the previous reservoir, initially present in the line between the new reservoir and the filter previously equilibrated with fluid from the new reservoir, from contaminating the previously equilibrated (new) filter.
***As noted in discussion, SR32 activation must follow a duty cycle initially, ending in permanent activation of SR32 until end of use of R3. The duty cycle involves switching back and forth between solenoid patterns 12 and 13 as dictated by the duty cycle requirements.

The number of reservoirs could be less than or greater than the number specified here, with corresponding changes in solenoid number. Furthermore, the number of layers of R1–R4 need not conform to the descriptions given above. The limits would be one reservoir at the least and perhaps eight reservoirs at the maximum, in which any reservoir could have from one to four compartments. The upper limits are based partly on volume and crowding constraints and partly on the difficulty of imagining any procedure complex enough to require more reservoirs for its control.

Another variation would be to employ different capacity reservoirs at different positions (e.g., instead of the herein preferred embodiment, one might have a 2-liter reservoir followed by a one-liter reservoir followed by a 3-liter reservoir followed by a one-liter reservoir, and so on).

In principle, the use of individual reservoirs could be abandoned in favor of one multicompartment reservoir consisting of perhaps four to twenty concentric cylinders each activated by solenoids or even by manual levers external to the temperature-controlled area, all stirred by a single central stir table. Abrupt or step changes in concentration could still be accommodated if the stepped change is not delivered via the stirred central area. The relative positions of the reservoirs could also change.

The arterial concentration sensor could be located proximal to rather than distal to the origin of the organ loop in the circuit, but should not be located proximal to the filters.

A pressure sensor to sense pressure developing on the circuit pump side of the filters could be incorporated as a warning device.

DESCRIPTION OF THE METHOD

The complete cryopreservation method using the above-described apparatus comprises four parts. The first part consists of the pretreatment of the organ prior to its removal. The second part is the choice of cryoprotective agents. The third part is the actual protocol for introducing and removing the cryoprotectant. And the final part is treatment of the organ and the recipient upon organ transplantation.

Part I: Organ Pretreatment with Cytoprotective Drugs In vivo and Organ Procurement The donor is pretreated in the normal manner except for the infusion of iloprost, which is a relatively long-lived analogue of $PGI_2$. Iloprost has been found by the present inventors to be effective in blocking the toxicity of subsequently-encountered cryoprotectant after either intravenous infusion to the systemic circulation or when given directly into the artery (or portal vein) of specific organs of interest. The best mode dose of iloprost appears to be 25 micrograms/ kg given by either route, although direct intra-arterial infusion is presently preferred to maximize organ exposure to the agent while minimizing iloprost-mediated systemic hypotension. 15 μg/kg is also effective, but appears less effective than 25 μg/kg. Acceptable limits of iloprost concentration for this application are 5–75 μg/kg, depending on species, infusion rate, duration of operation, etc. Iloprost is infused over the course of 20 min; acceptable infusion duration limits are 1–60 min for cadaveric organ donors. In the latter, for example, an acceptable variation would be to infuse iloprost briefly to protect the organ from the warm ischemia of organ procurement and then to compensate for brief exposure by perfusing with iloprost-containing solution at elevated or cold temperatures for a sufficient time (5–40 min). The second variation is to infuse iloprost at relatively low concentration over a relatively long time (20–60 min) so as to minimize hypotension; donor infusions for longer than 60 min are impractical.

After iloprost pre-treatment in vivo, organs of interest are flushed in situ with cold Euro Collins solution, UW solution or a comparably effective solution either simultaneously or in a phased manner so as to stabilize all organs quickly and thereby avoid conflicts in organ procurement. (Should normothermic preservation techniques supersede hypothermic preservation for hearts, the heart can be flushed with warm rather than cold solution.) The flushing solution(s) should initially contain iloprost (1 μg/ml in best mode, acceptable limits being 0–10 μg/ml), anticoagulants (e.g., heparin, 10,000 units/liter in the present embodiment, acceptable variations being 1,000–20,000 units/liter), vasodilators (e.g., papaverine, 40–90 mg/liter in best mode, 0–80 mg/liter as acceptable limits) and other desired agents, but a second flushing solution should be used to wash out all of these agents as cooling and blood washout is completed. The excised organ (except for organs that are best maintained by normothermic perfusion) should be transferred to an iced bath of flush solution and transported to a perfusion machine capable of introducing and removing cryoprotectants in the fashion to be described.

Part 2: Cryoprotective Agents: Formulae of the Vitrification Solutions VS4, VS41A, VS5, and VS51A All experiments have been carried out using solutions known as VS4 or VS41A. VS4 is composed of dimethyl sulfoxide (D), formamide (F), and 1,2-propanediol (P) such that the mole ratio of D to F is 1:1, the total mass of D+F+P per liter is 490 grams, and the total mass of P per liter is 150 grams. Thus, per liter, D+F=340 grams, F=124.33 grams, and D=215.67 grams. This mixture of cryoprotectants is preferred based on the results described below. Acceptable variations for the proportions of D, F, and P are: D:F weight ratio can be as low as 1.4 and as high as 3.5; for the former, the proportion of P:(D+F) should be elevated to 18:34 and/or total concentration raised to 50–51% w/v (grams/deciliter) by addition of extra P.

At low cooling rates (5°–10° C./min) VS4 will vitrify at 1,000 atm of hydrostatic applied pressure but not at ordinary ambient pressures. The formula known as VS41A is required for use at ambient pressures ("1A" refers to 1 atmosphere). VS41A is prepared by multiplying all VS4 constituent masses by 55/49: thus, the total concentration of solutes in VS41A is 550 grams/liter vs the 490 grams/liter of VS4.

VS4 and VS41A appear to be particularly beneficial due to the exceptional ability of formamide to penetrate kidney tissue, the ability of dimethyl sulfoxide to block the toxicity of formamide, the beneficial balance between the three ingredients (maximizing vitrification tendency while minimizing both toxicity and total solute concentration), the lack of a colloid (typical colloid concentrations of about 4–7% w/v elevate viscosity unacceptably), the extraordinarily slow rate of devitrification of to these solutions at appropriate pressures (1,000 atm and 1 atm, respectively), and the good stability of VS41A at $-135°$ C. during at least 6 months of storage.

The cryoprotectants used for organ perfusion are to be adjusted between the limits represented by VS4 and VS41A, depending upon the organ's tolerance to high pressures and the organ's tolerance to high cryoprotectant concentrations, so as to optimize the tradeoff between pressure and concentration required to maintain vitrifiability. For example, an organ that cannot tolerate 1,000 atm but that can tolerate 500 atm should be perfused with a solution intermediate between VS4 and VS41A (i.e., total grams of D+F+P per liter=520), with the relative proportions of D, F, and P remaining unchanged. Very large organs that require extremely slow cooling rates at ambient pressure should be perfused with concentrations in excess of 550 grams/liter, to a maximum of about 600 grams/liter, to ensure vitrifiability at these very low cooling rates at ambient pressure. At elevated pressures, similar proportional increases in solute concentration will be required as cooling rate is lowered.

Recent experiments (see results below) with kidney slices indicate that a formula identical to that of VS4 but with 2,3-butanediol replacing 1,2-propanediol, wherein 2,3-butanediol consists of a mixture of the dextro- and levorotatory forms with minimal meso form present (<5% w/w), provides viability identical to the viability obtained with VS4. This formula, known as VS5, may have greater stability than VS4. Similarly, VS51A is composed as per the above description of VS41A, except for the replacement of 1,2-propanediol by dextrose and levorotatory isomers of 2,3-butanediol (<5% w/w meso form). Variations between VS5 and VS51A are to be used as per the descriptions above for VS4 to VS41A.

All cryoprotectant solutions must contain, in addition to the cryoprotectants themselves, slowly-penetrating solutes comprising the "carrier" or "vehicle" solution for the cryoprotectants. Typical examples would be UW solution, Euro Collins solution, or Renal Preservation Solution 2 (RPS-2). Euro Collins and possibly RPS-2 are believed to be superior to UW as carrier solutions for kidneys, whereas the opposite is likely to be true for livers, and hearts may do best with none of these particular carriers. The best mode process uses Euro Collins as the carrier solution of choice.

Part 3: protocol for Cryoprotectant Introduction and Removal

Figure 5:
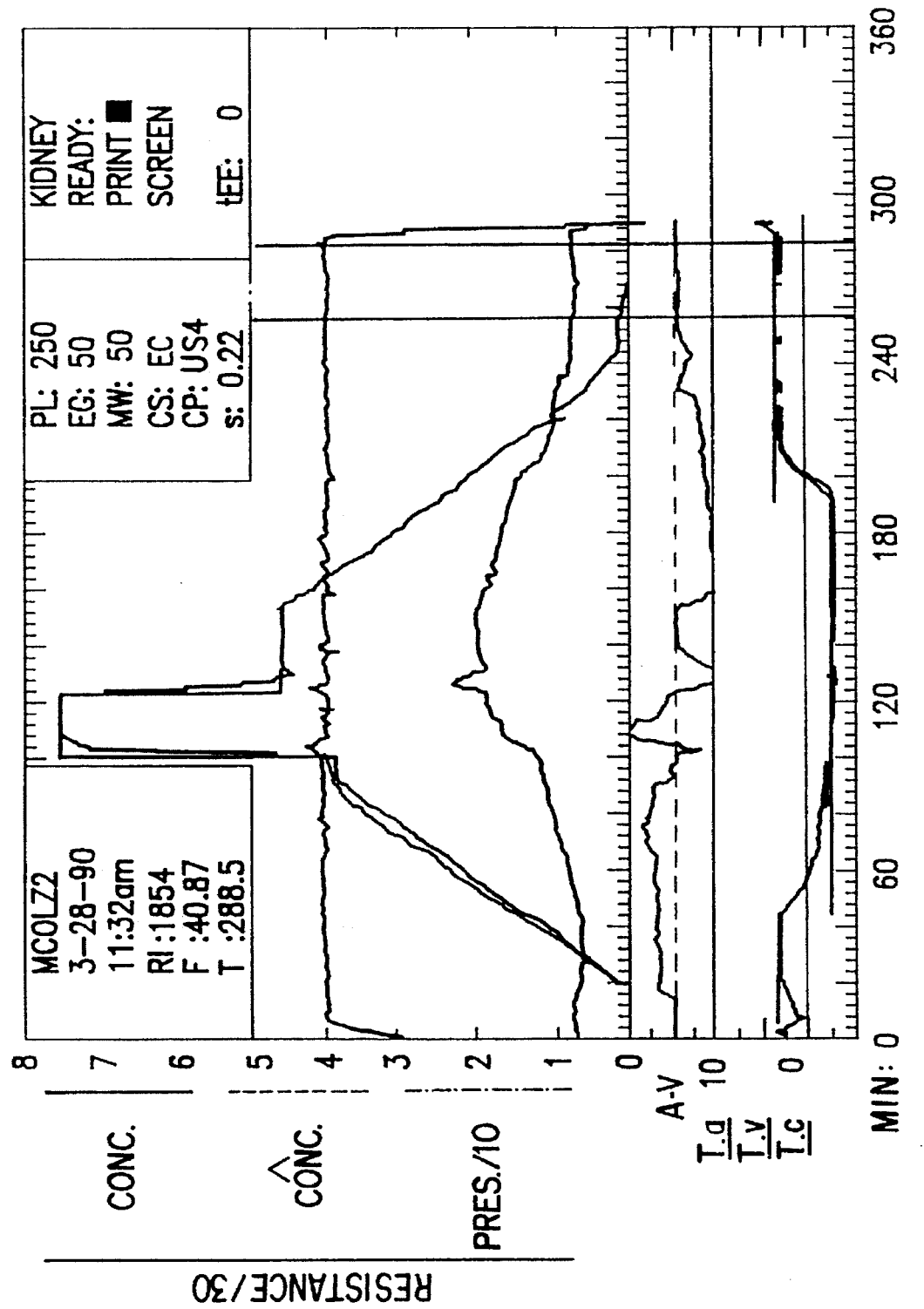
FIG. 5 shows the appearance of a typical protocol for introducing and removing cryoprotectant as viewed on the computer monitor during a perfusion.
Figure 6A:
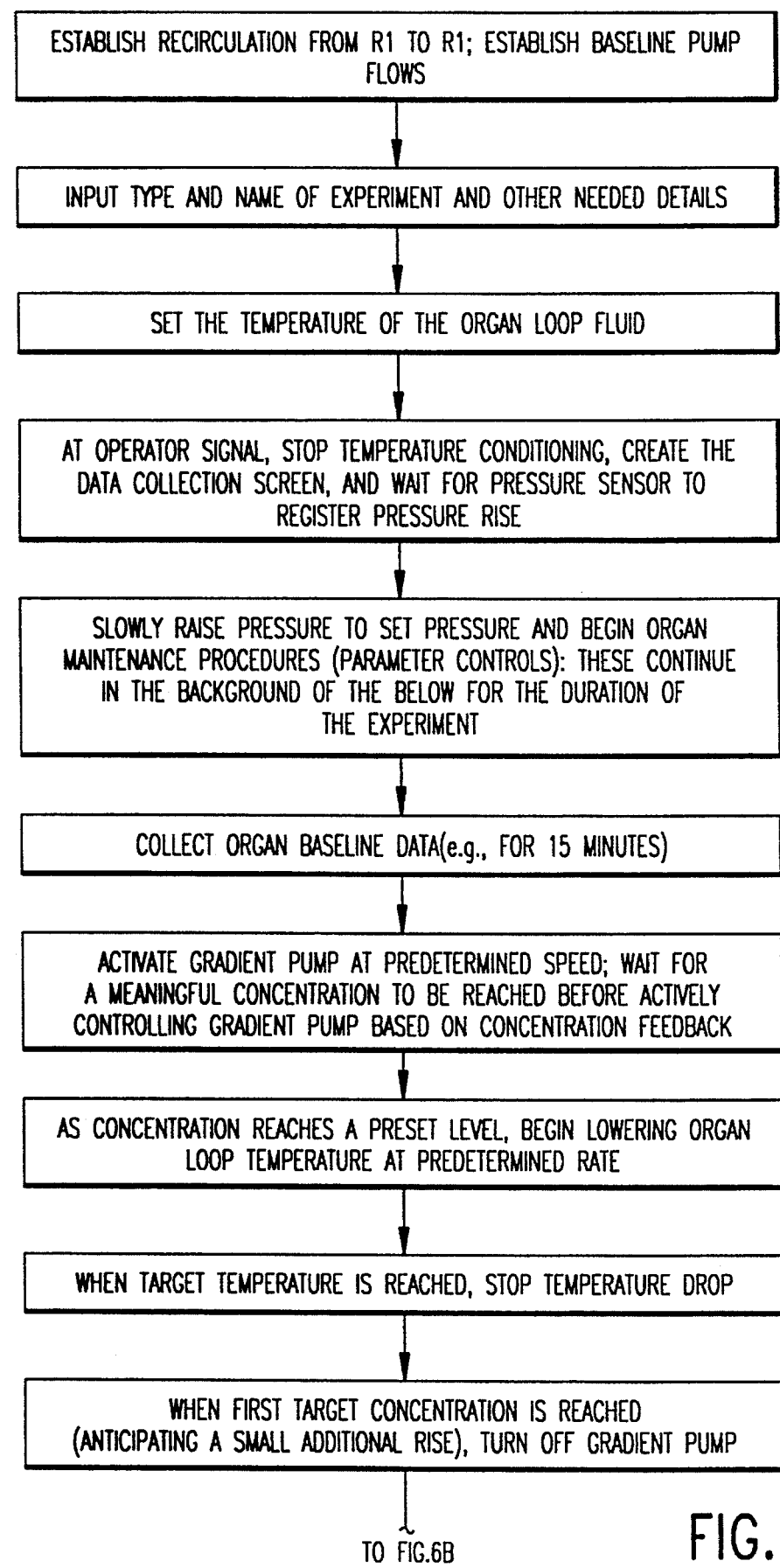
Figure 6B:
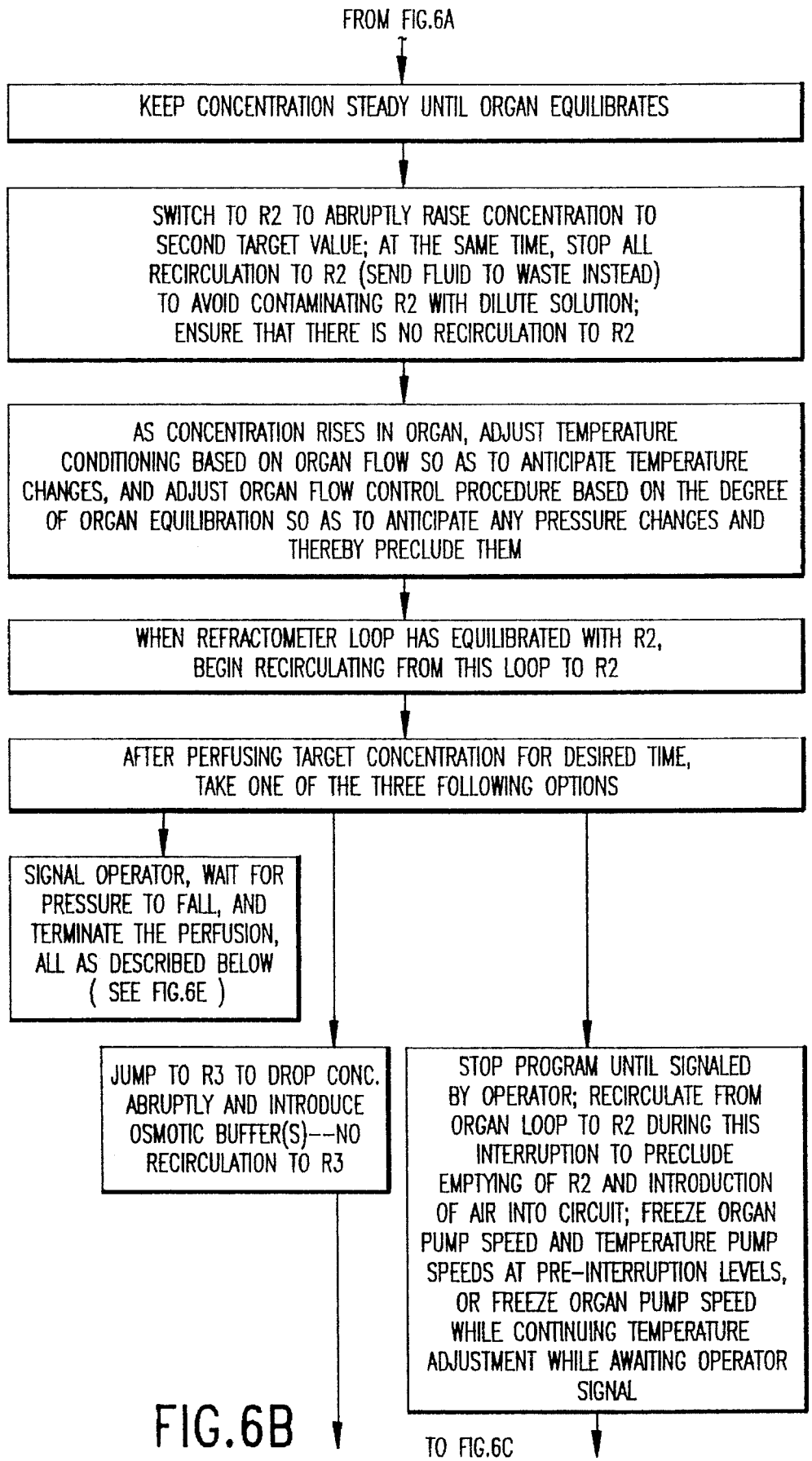
Figure 6C:
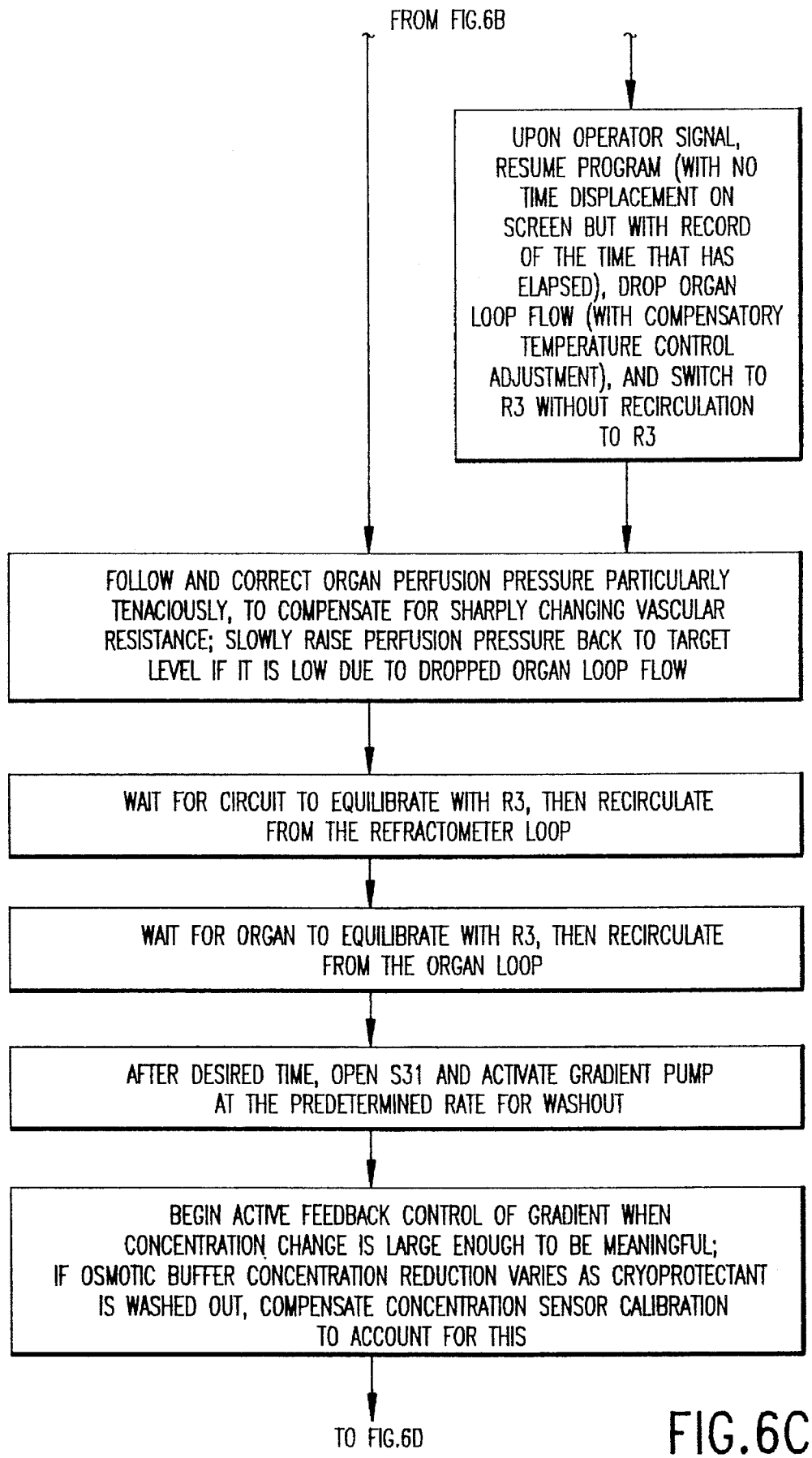

A typical protocol for cryoprotectant introduction and removal presently in use in the present inventors' laboratory and yielding reliable, high-quality survival of rabbit kidneys after cryoprotectant washout, transplantation, and long-term functional and histological follow-up, is shown in FIG. 5 and described in more detail in the flow charts of FIGS. 6A–E.

Perfusion pressure. The organ is perfused at pressures sufficient to overcome the organ's critical closing pressure but otherwise low enough to avoid needless damage to the vascular tree. The best mode perfusion pressure is 40 mmHg, without significant pulsation. A desirable range of acceptable pressures has been found to be 20–70 mmHg for different species, including man.

Initial perfusion. In the best mode protocol, perfusion is first carried out for 15 min to establish baseline values for vascular resistance, to establish calibrations (for pressure and refractive index), to ensure complete blood washout, and to thermally equilibrate the organ. Clinically, the initial perfusion time is arbitrary, and can be adjusted (from zero minutes to 1–2 days or more) to meet the requirements of the organ procurement and transportation process. In the inventors' laboratory, the perfusate in this period is Euro Collins solution. However, this initial perfusate could also be UW solution or other stabilizing solution in a clinical setting depending upon the needs of the hospital or procurement team.

Initial temperature. Initial perfusion temperature required for organ procurement and transportation need not be identical to the perfusion temperature established just before introduction of cryoprotectant. For example, most organs may be shipped while surrounded by crushed ice at 0° C. while other organs may be shipped while being perfused at normothermia (37° C.). When organs are ready for cryoprotectant administration, however, a preselected, standardized perfusion temperature is established. In the best mode process, initial perfusion temperature is 3.5°–4° C., and the acceptable limits are 0°–15° C. The inventors consider that organs requiring normothermic perfusion for best long-term maintenance can nevertheless be cooled to within this same temperature range and treated in a manner similar to that of hypothermically-preserved organs without damage within the relatively short times required for this process.

First elevation of cryoprotectant concentration. Following the initial baseline perfusion, cryoprotectant concentration is elevated at a constant rate until a first plateau of concentration is established. When using a VS4-type mixture of cryoprotectants, the proportions of different cryoprotectants in the mixture are held constant while total concentration is allowed to change. The rate of increase in total concentration for VS4type solutions is set to 51 mM/min (3.06 M/hr) in the best mode process, acceptable variations being 35–75 mM/min. These rates are considerably in excess of the 30 mM/min rates used by known techniques for glycerol and propylene glycol which are considered to be unnecessarily and undesirably slow for vitrification solution solutes. Linear elevation of concentration promotes equilibration without creating unnecessarily large osmotic stresses.

First concentration plateau. The first plateau is set in the best mode process at 25% w/v total cryoprotectant (250 grams/liter, or about 3.8 molar), acceptable variations being 20–32% w/v or w/w. The first plateau should be set to a level that is close to half the concentration of the final vitrification solution: lower first plateau levels will increase osmotic stress upon subsequent perfusion with vitrification solution, whereas substantially higher first plateau levels will produce increased toxicity due to longer exposure times to concentrated cryoprotectant. The duration of the first plateau is set to 10 min in the best mode procedure, acceptable variations being 5–30 min, depending on perfusion pressure (and thus organ flow rate), vascular resistance, and organ permeability to cryoprotectant. The duration should be great enough to allow the organ to osmotically equilibrate with the arterial perfusate, as indicated by a zero (or virtually zero) arterio-venous concentration difference, to minimize unnecessary osmotic stress during the subsequent jump to vitrification solution.

Temperature reduction during first concentration rise. During concentration elevation, temperature is simultaneously lowered to protect the organ from chemical toxicity of the cryoprotectant. In the best mode process, temperature reduction begins as the arterial cryoprotectant concentration reaches 1.3 molar; acceptable limits are 0.5 molar to 3.5 molar. Temperature descent is terminated as the arterial concentration reaches the first concentration plateau (as noted above, 25% (3.8M) in the best mode procedure and 20–32%, or about 3–4.9M for VS4 solutes, within the process limits). The concentration change during cooling is thus about 2.5M in the best mode process and may vary from about 1M to 4.4M.

As noted above, pre-cooling temperature should fall within the limits of 0°–15° C. The temperature after cooling should fall within the range of −13° C. to +5° C. Cooling should not continue to below the freezing point of the organ. In the best mode process, final temperature is presently −1.5° C., representing a fall of 5° C. from the initial temperature and a cooling rate of about 0.25° C./min. The maximum cooling rate possible within the above limits is about 2.1° C./min, which should be slow enough to avoid possible thermal shock to the organ. Minimum temperature drop during cooling is 2° C., maximum temperature drop is 28° C.

Perfusion with vitrification solution, second concentration plateau. A step change in concentration from the first concentration plateau to the vitrification solution is necessary to control exposure time to highly concentrated cryoprotectant. In the best mode procedure, the concentration of vitrification solution is, as noted above, 490–550 grams/liter or about 7.5–8.4 molar for VS4-type solutions (extending as high as 600 grams/liter for hard-to-vitrify materials such as livers).

For VS5-type solutions, the final concentrations may be reduced slightly, to about 480–540 grams/liter. For non-VS4-type vitrification solutions, the concentration limits for the present process are 40%–60% w/v cryoprotectant. Concentration is held steady at the vitrifiable concentration for 20 min in the best mode procedure, acceptable variations being 10–50 min. Concentration must be held steady sufficiently long for the removal of non-vitrifiable water from the cells and from the interstitial spaces, i.e., long enough for the organ to closely approach osmotic equilibrium with the perfusate.

Temperature during perfusion with vitrification solution. In the best mode procedure, temperature is held constant at 0° to −5° C. (the temperature of choice presently being −1.5° C.) as concentration rises to vitrifiable levels. Temperature constancy rather than renewed temperature descent is desirable to control viscosity: as viscosity rises with temperature reduction, effective organ resistance must also increase, reducing organ osmotic equilibration rates, necessitating increased organ exposure times to the cryoprotectant, and possibly exerting greater damage to the vascular endothelium. Lower temperatures also increase the likelihood of "chilling injury". However, an acceptable variation would be to further lower temperature as the jump to vitrification solution commences or shortly thereafter, particularly for organs perfused at or near the high temperature limits up to this point and particularly for concentrations above 49% w/v and organs that are particularly susceptible to cryoprotectant toxicity and require lower temperatures to suppress this toxicity. Although VS41A and VS51A have freezing points close to −40° C., perfusion to temperatures this low are not included in the present process, since temperatures this low appear unnecessary, cumbersome, and most likely counterproductive. The low-temperature limit of the process is therefore set during vitrification solution perfusion at only −20° C. and +5° C. is retained as the upper limit, permitting limited additional cooling during vitrification solution perfusion.

The next step of any practical vitrification procedure will be to remove the organ from the perfusion machine and cool it to cryogenic temperatures, with or without prior pressurization. After the organ is warmed, however, it will have to be placed back into the perfusion machine to resume the type of perfusion protocol shown in FIG. 5 at the beginning of the third concentration plateau.

First concentration reduction: third concentration plateau. The choice of concentration for the third concentration plateau in the best mode protocol is 30% w/v (300 grams/liter; 4.6M) VS4 solutes (D, F, and P in the usual proportions), acceptable variations being 20–35% (w/v or w/w) cryoprotectant (roughly 3 to 5.5M). The concentration at this stage should not be less than 40% (2/5) of the concentration of the vitrification solution in order to avoid osmotic damage; in the best mode process, the concentration at the third plateau is over 3/5 of the concentration at the second plateau.

An "osmotic buffering agent" (non-penetrating extracellular low-molecular-weight solutes that counteract the osmotic effect of greater intracellular vs extracellular concentrations of cryoprotectant during the cryoprotectant efflux process) is present in the third plateau perfusate (although not shown in FIG. 5). Preferred osmotic buffering agents are raffinose or sucrose. Although mannitol has been used successfully in virtually all of the inventors' experiments, mannitol has been found to penetrate renal cells with resulting detrimental effects. Mannitol and even sucrose will not be workable for the liver, either, since its cells are much more permeable to both solutes than are most mammalian organs' cells.

Osmotic buffer concentration in the best mode 30% washout plateau solution is 250 mM. In protocol variations employing lower third plateau concentrations (e.g., 20% w/v cryoprotectant), more osmotic buffer is required (to an upper limit of 1,000 mM). In variations employing higher third plateau concentrations (e.g., 35% w/v cryoprotectant), less osmotic buffer is required (to a lower limit of about 150 mM). The presence of osmotic buffer within these limits is required to counteract the otherwise-fatal osmotic effects of a large stepwise drop in penetrating cryoprotectant concentration. The duration of the third concentration plateau is 16 min in the best mode process (acceptable limits=5–40 min), which is just enough time for osmotic equilibration of the organ with the washout perfusate.

Temperature during the third concentration plateau. The choice of perfusion temperature during the third plateau depends on the previous thermal history. In the best mode process, perfusion temperature is retained at −1.5° C. The only cases in which the temperature will be different during the second and third concentration plateaus is in variations in which temperature is reduced during second plateau perfusion to values below or near the freezing point of the third plateau perfusate or when chilling injury requires additional warming to minimize overall damage. In these variations, the temperature of the third plateau perfusate is set to the minimum value consistent with minimizing damage, and the organ is warmed to this temperature before being perfused with perfusate at the concentration of the third plateau.

Gradual concentration reduction to zero: The next stage in the process is the gradual reduction of cryoprotectant concentration to zero or virtually zero. In the best mode process, this is carried out at a constant rate of about −43 mM/min (acceptable variations being −31 to −65 m M/min). Non-constant declining concentration schedules (rapid fall at high concentrations, slower fall at lower concentrations) are also an acceptable variation, e.g., a linear fall at 1.5 times the average linear rate for the first third of the washout followed by a linear fall at 0.86 times the average linear rate for the second two-thirds of the washout.

As penetrating cryoprotective agent concentrations fall, the concentration of osmotic buffer also falls in proportion, reaching a final nonzero concentration of osmotic buffer when penetrating cryoprotectant concentration reaches zero. This final nonzero concentration of osmotic buffer is 50 mM in the best mode process and may acceptably vary from 25 mM to 500 mM. During reduction of cryoprotectant concentration, absolute transmembrane osmotic forces attributable to the cryoprotectant transmembrane concentration gradient become reduced, thus reducing the requirement for osmotic buffering. Reducing osmotic buffer concentration during cryoprotectant washout is therefore designed to minimize osmotic damage from the osmotic buffer both during cryoprotectant washout and thereafter and is further designed to reduce potential cellular uptake of nominally non-penetrating osmotic buffering agent. No previous perfusion technique of cryoprotectant washout has ever made use of the "declining osmotic buffer principle".

Temperature control during gradual cryoprotectant washout. During cryoprotectant washout, temperature is elevated to facilitate washout, reduce osmotic forces, and restore a perfusion temperature appropriate for an organ containing no cryoprotectant. In the best mode process, temperature elevation begins as concentration falls to 4.7 molar and continues linearly with concentration drop until the initial perfusion temperature is reached when arterial concentration reaches 1.3 to 0.8M (1° C. per 0.68 to 0.78M rise in concentration; 3.4–3.9M concentration change during warming). Acceptable variations for the concentration at which temperature initially rises are 2.5–5.5M and for the concentration at which temperature rise is completed are 0.5M–4.5M.

Osmotic buffer washout. The final step in the process is to wash out the osmotic buffer. In the current best mode process, 50 mM sucrose is attained at the end of cryoprotectant washout. Although it is acceptable to leave such low concentrations of osmotic buffer in the organ during short holding times before transplantation, interstitial osmotic buffer (OB) is expected to cause osmotic expansion of the interstitial space during blood reflow, with consequent temporary reduction in organ perfusion in vivo. This effect will become unacceptable at higher OB concentrations (>100 mM) and will necessitate OB washout before transplantation. A further problem with leaving OB in the organ for extended times before transplantation is potential leakage of OB into organ cells with consequent cellular swelling and reduced perfusion upon transplantation. The inventors have typically washed out 50 mM mannitol over the course of 30 min with complete success upon transplantation. Higher concentrations of OB (up to 500 mM) may be washed out over more extended times (30–90 min) that depend on perfusion resistance response to OB dilution. For clinical purposes, the duration of the post-washout perfusion period, comprising the osmotic buffer washout plus subsequent perfusion with no osmotic agent, is adjustable to fit the logistic requirements of organ transportation and transplantation.

Part 4: Treatment of the Organ and the Recipient at the Time of Transplantation and Thereafter It is essential that the recipient receive aspirin (acetylsalicylate, 1–3 mg/kg) and heparin (100–250 units/kg) shortly before release of the vascular clamps, both higher and lower concentrations resulting in vascular obstruction and failure. The best mode concentrations are 2 mg/kg and 200 units/kg, respectively. It may also be helpful to gradually re-infuse iloprost (5–40 µg/kg, IV) beginning 5 min before clamp release and continuing for at least an additional 15 min, to obviate reperfusion injuries such as damage resulting from temporary hypoxia and inflammatory responses. The best mode method involves the infusion of 7–10 µg/kg of iloprost IV beginning 5 min before revascularization and continuing until 15 min after revascularization. No benefit has been observed from the use of calcium channel blockers.

Process for Control (Non-Cryoprotectant) Perfusions.

Figure 7A:
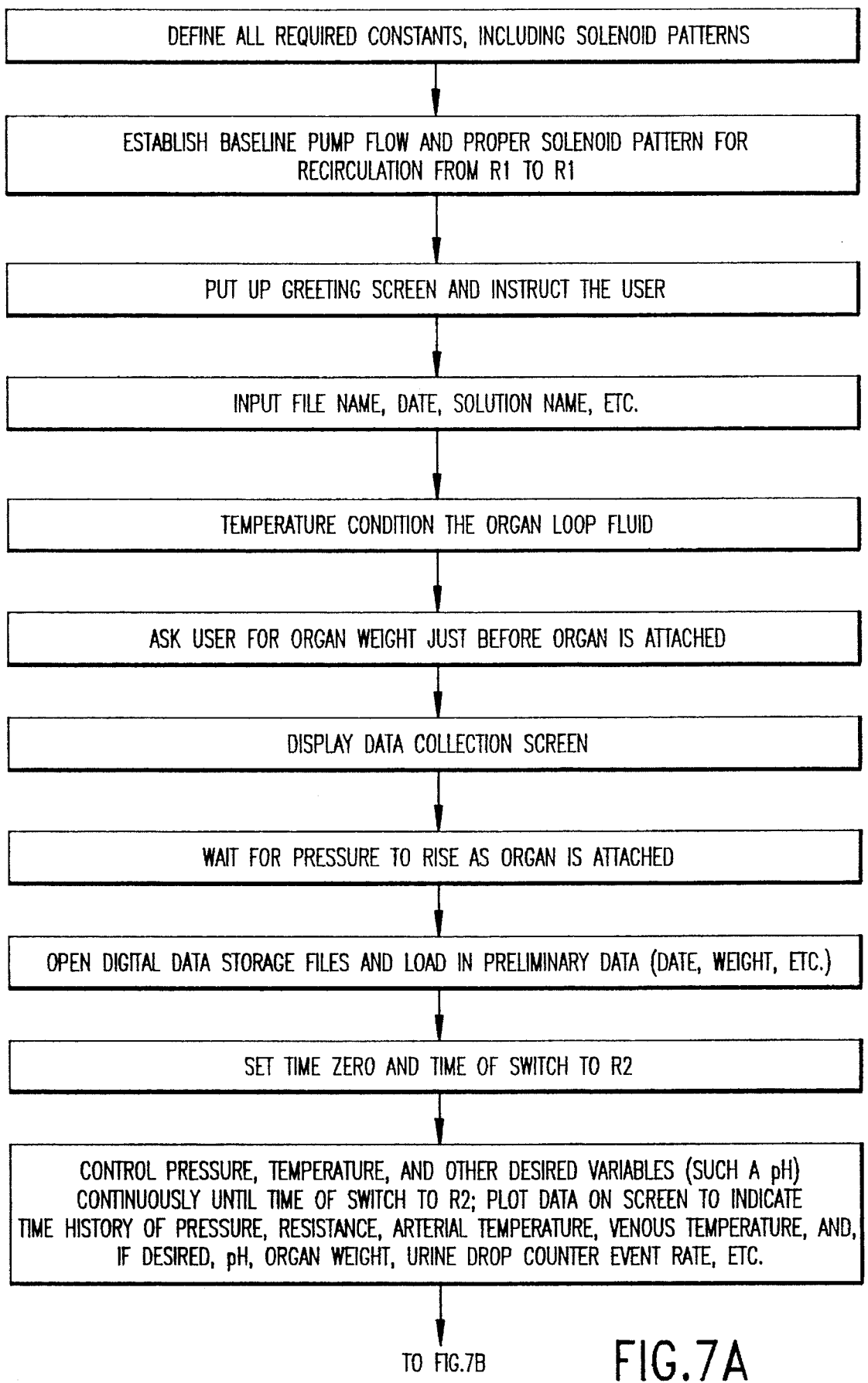

The equipment described here is capable of creating, besides organ cryoprotection protocols, a wide varitey of protocols for conventional organ hypothermic and normothermic preservation. In addition, a wide variety of normothermic pharmacological, physiological, and pathophysiological protocols are possible. The present inventors exemplify many of these possibilities by describing the steps required to carry out many of these protocols in FIGS. 7A–7B, which are self-explanatory.

Results

FIG. 8 shows post-operative serum creatinines of rabbits receiving kidneys previously perfused with VS4 in Euro-Collins solution. Prior to procurement, organs were treated in vivo with zero, 15, and 25 µg/kg of iloprost given by systemic intravenous infusion over a 20-minute period. Kidneys in these three groups were exposed to VS4 at +2, 0–2, and −1° to 6° C., respectively. Initial and final perfusion temperatures were 2° C. in all cases. Rabbit survivals in these three groups were 5/16 (31%), 6/10 (60%), and 10/10 (100%), respectively. Only data for rabbits surviving the first night after surgery are included. Rabbit survivals depended entirely on the function of the kidney previously perfused with VS4: a contralateral nephrectomy was performed at the time of transplantation, and no support by dialysis was attempted. Histology at long-term follow-up in these rabbits was poor without iloprost, marginal with the lower dose of iloprost, and normal with the higher dose of iloprost and the lowest perfusion temperatures. The results of control (no cryoprotectant) perfusions with Euro Collins are included in FIG. 8 as well (bottom curve). Although damage in the best VS4 group is greater than in the controls, all damage appears to be fully reversible within a short time postoperatively.

TABLE I

Viability of Kidney slices Treated with VS4 vs. VS5

Treatment K/Na ratio of tissue (mean +/– SEM)

| | |
|---|---|
| VS4 | 3.43 +/– 0.07 |
| VS5 | 3.27 +/– 0.12 |
| $p > 0.05$ | |

K/Na ratio measured after washing out the cryoprotectants and incubating the cortical slices at 25° C. for 90 minutes to permit active transport of $K^+$ and $Na^+$.

While various embodiments of the present invention have been described above, it should be understood that they have been presented by way of example, and not limitation. Thus the breadth and scope of the present invention should not be limited by any of the above described exemplary embodiments, but should be defined only in accordance with the following claims and their equivalents. It will be understood by those skilled in the art that various changes in form and detail may be made therein without departing from the spirit and scope of the invention.

What is claimed is:

1. A computer controlled apparatus for perfusing a biological organ, comprising:

a programmable computer;

a plurality of arterial perfusate reservoirs, each having an input and an output;

means coupled to said computer and to said reservoirs for selectively sampling the contents of said reservoirs under the control of said computer;

means for varying the concentrations of chemical agents in the arterial perfusate;

means for generating increasing or decreasing concentration-time profiles of the chemical agents in the arterial perfusate to elevate the concentration of the chemical agents in the perfusate to any desired level and to return the concentration of the chemical agents to or approximately to zero;

an organ container for holding a biological organ;

a recirculating fluid flow path connecting selected outputs and the inputs of the plurality of reservoirs;

an organ flow path extending from the recirculating flow path, through an organ pump, to the organ container;

said organ pump being located in said organ flow path and coupled to and controlled by said computer for withdrawing fluid from the recirculating flow path and delivering said fluid to one or more organs in said organ flow path, thereafter to one of said reservoirs, to the recirculating flow path or to said waste outlet, according to control instructions received from said computer;

first sensor means for determining the concentrations of chemical agents in the fluid flow paths and for determining the uptake of these agents by the one or more organs in said organ flow path;

second sensor means coupled to the computer and interposed in at least one of the recirculating and organ flow paths, for sensing at least one of the temperature, pH, and pressure of the fluid in the flow paths and to provide the sensed information to the computer;

main pump means interposed in said recirculating flow path and optionally coupled to and controlled by said computer for circulating fluid from a selected reservoir through said recirculating fluid flow path and through said sensor means, as determined by control instructions received from said computer;

means for selectively returning perfusate to a selected one of said reservoirs from the recirculating flow path or to a waste outlet as a function of information sensed by at least one of said first and second sensors; and a temperature-controlled cabinet for housing the reservoirs, flow paths and pumps to maintain organ and perfusate temperatures at desired levels.

2. The apparatus defined in claim 1, further comprising a temperature conditioning apparatus interposed in the recirculating flow path.

3. The apparatus defined in claim 1, further comprising a plurality of temperature sensors distributed along the flow paths and connected the computer, whereby the computer can monitor the temperature of the liquid in the flow paths at various points.

4. The apparatus defined in claim 3, further including a refractometer interposed in the recirculating flow path and connected to the computer.

5. The apparatus defined in claim 4, further comprising a plurality of valves interposed in the recirculating flow path upstream of the plurality of reservoirs, the valves electrically connected to and controlled by the computer and configured to selectively direct a liquid in the recirculating flow path to one or more of the reservoirs or to said waste outlet.

6. The apparatus defined in claim 1, further comprising means located upstream of and in the second flow path for mixing perfusate prior to perfusing an organ contained in said organ container.

7. The apparatus defined in claim 1, wherein said first sensor means comprises means for measuring the difference in concentration of chemicals entering and exiting said organ container.

8. The apparatus defined in claim 1, wherein said second sensor means comprises:

first temperature measuring means disposed on the input side of said organ container for measuring the temperature of fluids entering said organ container; and second temperature measuring means disposed on the output side of said organ container for measuring the temperature of fluids exiting said organ container.

9. The apparatus defined in claim 8, further comprising temperature conditioning means coupled to said programmable computer and interposed in the organ flow path for adjusting the temperature of fluid flowing in said organ flow path as a function of the temperatures measured by said first and second temperature measuring means.

10. The apparatus defined in claim 1, further comprising valve means interposed in the fluid flow path containing said organ container and coupled to said programmable computer for selectively recirculating fluids in said fluid flow path or discarding said fluids to waste through said waste outlet.

11. The apparatus of claim 1, wherein the means for changing concentration time profiles comprises at least one gradient forming reservoir in combination with a pump for discharging fluid in said recirculating fluid flow path to said waste outlet.

12. The apparatus of claim 1, wherein the first sensor means comprises a refractometer.

13. The apparatus of claim 1, further comprising a differential refractometer for determining the difference in chemical concentrations between the arterial and venous sides of an organ in said organ flow path.

14. The apparatus of claim 1, further comprising at least one heat exchanger for optimizing temperature control of an organ during perfusion thereof.

15. The apparatus according to claim 14, further comprising:

a first heat exchanger coupled in said recirculating flow path; and a second heat exchanger coupled in said organ flow path between said organ pump and said organ container.

16. The apparatus according to claim 1, further comprising: a bubble trap disposed in said organ flow path downstream of said organ pump.

17. The apparatus according to claim 16, wherein said bubble trap has a volume sufficiently large to reduce the pulsatile action of said organ pump to a minimum and sufficiently small to minimize the liquid volume present in said bubble trap.

* * * * *